United States Patent
Parker

(10) Patent No.: US 12,285,263 B2
(45) Date of Patent: Apr. 29, 2025

(54) ASSESSING NEURAL STATE FROM ACTION POTENTIALS

(71) Applicant: Saluda Medical Pty Ltd, Artarmon (AU)

(72) Inventor: John Louis Parker, Artarmon (AU)

(73) Assignee: Saluda Medical Pty Ltd, Macquarie Park (AU)

( * ) Notice: Subject to any disclaimer, the term of this patent is extended or adjusted under 35 U.S.C. 154(b) by 245 days.

(21) Appl. No.: 17/804,846

(22) Filed: May 31, 2022

(65) Prior Publication Data

US 2022/0287620 A1    Sep. 15, 2022

Related U.S. Application Data

(63) Continuation of application No. 15/129,407, filed as application No. PCT/AU2015/050135 on Mar. 27, 2015, now abandoned.

(30) Foreign Application Priority Data

Mar. 28, 2014  (AU) .................................. 2014901110

(51) Int. Cl.
*A61B 5/00* (2006.01)
*A61B 5/24* (2021.01)
(Continued)

(52) U.S. Cl.
CPC ............ *A61B 5/4076* (2013.01); *A61B 5/388* (2021.01); *A61B 5/4041* (2013.01); *A61B 5/407* (2013.01);
(Continued)

(58) Field of Classification Search
CPC ........... A61B 5/742–745; A61B 5/7271–7275; A61B 5/112; A61B 5/1117;
(Continued)

(56) References Cited

U.S. PATENT DOCUMENTS 3,724,467 A    4/1973 Avery et al.
3,736,434 A    5/1973 Darrow
(Continued)

FOREIGN PATENT DOCUMENTS

AU    2013277009 B2    1/2016
CN    103648583 A    3/2014
(Continued)

OTHER PUBLICATIONS

Communication Pursuant to Article 94(3) EPC, for European Patent Application No. 14861553.7, Dated Nov. 4, 2022, 8 Pgs.
(Continued)

*Primary Examiner* — Benjamin S Melhus
(74) *Attorney, Agent, or Firm* — Barnes & Thornburg LLP

(57) ABSTRACT

The neural health or state of a subject is assessed. A recording is obtained of a compound action potential arising in neural tissue of the subject. The recording is processed to determine whether a profile of the recorded compound action potential is anomalous, such as by exhibiting doublets, peak broadening or deformation, or other anomaly. An indication is output regarding the neural state of the subject based on determined anomalies in the recorded compound action potential.

20 Claims, 9 Drawing Sheets

(51) Int. Cl.
*A61B 5/388* (2021.01)
*A61N 1/36* (2006.01)

(52) U.S. Cl.
CPC .......... *A61B 5/4824* (2013.01); *A61B 5/4836* (2013.01); *A61N 1/36071* (2013.01); *A61N 1/36135* (2013.01); *A61N 1/36185* (2013.01)

(58) Field of Classification Search
CPC ....... G16H 30/20–40; G16H 40/60–67; G16H 10/20; G16H 50/30; G06T 7/20; G06T 7/70; G06V 40/23; G06V 40/25
See application file for complete search history.

(56) References Cited

U.S. PATENT DOCUMENTS

| | | |
|---|---|---|
| 3,817,254 A | 6/1974 | Maurer |
| 3,898,472 A | 8/1975 | Long |
| 4,158,196 A | 6/1979 | Crawford, Jr. |
| 4,418,695 A | 12/1983 | Buffet |
| 4,474,186 A | 10/1984 | Ledley et al. |
| 4,628,934 A | 12/1986 | Pohndorf et al. |
| 4,807,643 A | 2/1989 | Rosier |
| 4,856,525 A | 8/1989 | Van Den Honert |
| 5,113,859 A | 5/1992 | Funke |
| 5,139,020 A | 8/1992 | Koestner et al. |
| 5,143,081 A | 9/1992 | Young et al. |
| 5,156,154 A | 10/1992 | Valenta et al. |
| 5,172,690 A | 12/1992 | Nappholz et al. |
| 5,184,615 A | 2/1993 | Nappholz et al. |
| 5,188,106 A | 2/1993 | Nappholz et al. |
| 5,215,100 A | 6/1993 | Spitz et al. |
| 5,324,311 A | 6/1994 | Acken |
| 5,417,719 A | 5/1995 | Hull et al. |
| 5,431,693 A | 7/1995 | Schroeppel |
| 5,458,623 A | 10/1995 | Lu et al. |
| 5,476,486 A | 12/1995 | Lu et al. |
| 5,497,781 A | 3/1996 | Chen et al. |
| 5,638,825 A | 6/1997 | Yamazaki et al. |
| 5,702,429 A | 12/1997 | King et al. |
| 5,758,651 A | 6/1998 | Nygard et al. |
| 5,776,170 A | 7/1998 | Macdonald et al. |
| 5,785,651 A | 7/1998 | Kuhn et al. |
| 5,792,212 A | 8/1998 | Weijand et al. |
| 5,814,092 A | 9/1998 | King |
| 5,895,416 A | 4/1999 | Barreras et al. |
| 5,913,882 A | 6/1999 | King |
| 5,999,848 A | 12/1999 | Gord et al. |
| 6,020,857 A | 2/2000 | Podger |
| 6,027,456 A | 2/2000 | Feler et al. |
| 6,038,480 A | 3/2000 | Hrdlicka et al. |
| 6,066,163 A | 5/2000 | John |
| 6,114,164 A | 9/2000 | Dennis et al. |
| 6,144,881 A | 11/2000 | Hemming et al. |
| 6,157,861 A | 12/2000 | Faltys et al. |
| 6,212,431 B1 | 4/2001 | Hahn et al. |
| 6,246,912 B1 | 6/2001 | Sluijter et al. |
| 6,381,496 B1 | 4/2002 | Meadows et al. |
| 6,449,512 B1 | 9/2002 | Boveja |
| 6,463,328 B1 | 10/2002 | John |
| 6,473,649 B1 | 10/2002 | Gryzwa et al. |
| 6,473,653 B1 | 10/2002 | Schallhorn et al. |
| 6,493,576 B1 | 12/2002 | Dankwart-Eder |
| 6,516,227 B1 | 2/2003 | Meadows et al. |
| 6,522,932 B1 | 2/2003 | Kuzma |
| 6,600,955 B1 | 7/2003 | Zierhofer et al. |
| 6,658,293 B2 | 12/2003 | Vonk et al. |
| 6,675,046 B2 | 1/2004 | Holsheimer |
| 6,782,292 B2 | 8/2004 | Whitehurst |
| 6,895,280 B2 | 5/2005 | Meadows et al. |
| 6,898,582 B2 | 5/2005 | Lange et al. |
| 6,909,917 B2 | 6/2005 | Woods et al. |
| 7,089,059 B1 | 8/2006 | Pless |
| 7,171,261 B1 | 1/2007 | Litvak et al. |
| 7,177,675 B2 | 2/2007 | Suffin et al. |
| 7,206,640 B1 | 4/2007 | Overstreet |
| 7,231,254 B2 | 6/2007 | DiLorenzo et al. |
| 7,286,876 B2 | 10/2007 | Yonce et al. |
| 7,412,287 B2 | 8/2008 | Yonce et al. |
| 7,450,992 B1 | 11/2008 | Cameron |
| 7,634,315 B2 | 12/2009 | Cholette |
| 7,734,340 B2 | 6/2010 | De Ridder |
| 7,742,810 B2 | 6/2010 | Moffitt |
| 7,792,584 B2 | 9/2010 | Van Oort et al. |
| 7,818,052 B2 | 10/2010 | Litvak et al. |
| 7,831,305 B2 | 11/2010 | Gliner |
| 7,835,804 B2 | 11/2010 | Fridman et al. |
| 7,890,182 B2 | 2/2011 | Parramon et al. |
| 7,894,905 B2 | 2/2011 | Pless et al. |
| 8,083,685 B2 | 12/2011 | Fagin et al. |
| 8,190,251 B2 | 5/2012 | Molnar et al. |
| 8,224,459 B1 | 7/2012 | Pianca et al. |
| 8,239,031 B2 | 8/2012 | Fried et al. |
| 8,249,698 B2 | 8/2012 | Mugler et al. |
| 8,332,047 B2 | 12/2012 | Libbus et al. |
| 8,359,102 B2 | 1/2013 | Thacker et al. |
| 8,401,655 B2 | 3/2013 | De Ridder |
| 8,417,342 B1 | 4/2013 | Abell |
| 8,454,529 B2 | 6/2013 | Daly et al. |
| 8,494,645 B2 | 7/2013 | Spitzer et al. |
| 8,515,545 B2 | 8/2013 | Trier |
| 8,588,929 B2 | 11/2013 | Davis et al. |
| 8,670,830 B2 | 3/2014 | Carlson et al. |
| 8,886,323 B2 | 11/2014 | Wu et al. |
| 9,044,155 B2 | 6/2015 | Strahl |
| 9,155,892 B2 | 10/2015 | Parker et al. |
| 9,302,112 B2 | 4/2016 | Bornzin et al. |
| 9,381,356 B2 | 7/2016 | Parker et al. |
| 9,386,934 B2 | 7/2016 | Parker et al. |
| 9,872,990 B2 | 1/2018 | Parker et al. |
| 9,974,455 B2 | 5/2018 | Parker et al. |
| 10,206,596 B2 | 2/2019 | Single et al. |
| 10,278,600 B2 | 5/2019 | Parker et al. |
| 10,368,762 B2 | 8/2019 | Single |
| 10,426,409 B2 | 10/2019 | Single |
| 10,500,399 B2 | 12/2019 | Single |
| 10,568,559 B2 | 2/2020 | Parker et al. |
| 10,588,524 B2 | 3/2020 | Single et al. |
| 10,588,698 B2 | 3/2020 | Parker et al. |
| 10,632,307 B2 | 4/2020 | Parker |
| 10,842,996 B2 | 11/2020 | Baru et al. |
| 10,849,525 B2 | 12/2020 | Parker et al. |
| 10,894,158 B2 | 1/2021 | Parker |
| 10,918,872 B2 | 2/2021 | Parker et al. |
| 11,006,846 B2 | 5/2021 | Parker et al. |
| 11,006,857 B2 | 5/2021 | Parker |
| 11,045,129 B2 | 6/2021 | Parker et al. |
| 11,110,270 B2 | 9/2021 | Parker et al. |
| 11,167,129 B2 | 11/2021 | Parker |
| 11,172,864 B2 | 11/2021 | Parker et al. |
| 11,179,091 B2 | 11/2021 | Karantonis et al. |
| 11,191,966 B2 | 12/2021 | Wah |
| 2002/0055688 A1 | 5/2002 | Katims |
| 2002/0099419 A1 | 7/2002 | Ayal et al. |
| 2002/0193670 A1 | 12/2002 | Garfield et al. |
| 2003/0032889 A1 | 2/2003 | Wells |
| 2003/0045909 A1 | 3/2003 | Gross et al. |
| 2003/0139781 A1 | 7/2003 | Bradley et al. |
| 2003/0153959 A1 | 8/2003 | Thacker et al. |
| 2003/0195580 A1 | 10/2003 | Bradley et al. |
| 2004/0088017 A1 | 5/2004 | Sharma et al. |
| 2004/0116978 A1 | 6/2004 | Bradley |
| 2004/0122482 A1 | 6/2004 | Tung et al. |
| 2004/0158298 A1 | 8/2004 | Gliner et al. |
| 2004/0225211 A1 | 11/2004 | Gozani et al. |
| 2004/0254494 A1 | 12/2004 | Spokoyny |
| 2005/0010265 A1 | 1/2005 | Baru Fassio et al. |
| 2005/0017190 A1 | 1/2005 | Eversmann et al. |
| 2005/0021104 A1 | 1/2005 | DiLorenzo |
| 2005/0065427 A1 | 3/2005 | Magill et al. |
| 2005/0070982 A1 | 3/2005 | Heruth et al. |
| 2005/0075683 A1 | 4/2005 | Miesel et al. |
| 2005/0101878 A1 | 5/2005 | Daly et al. |
| 2005/0107674 A1 | 5/2005 | Parthasarathy et al. |

(56) References Cited

U.S. PATENT DOCUMENTS

| | | |
|---|---|---|
| 2005/0113877 A1 | 5/2005 | Giardiello et al. |
| 2005/0137670 A1 | 6/2005 | Christopherson et al. |
| 2005/0149154 A1 | 7/2005 | Cohen |
| 2005/0192567 A1 | 9/2005 | Katims |
| 2005/0203600 A1 | 9/2005 | Wallace |
| 2005/0209655 A1 | 9/2005 | Bradley et al. |
| 2005/0216064 A1 | 9/2005 | Heruth et al. |
| 2005/0282149 A1 | 12/2005 | Kovacs et al. |
| 2006/0009820 A1 | 1/2006 | Royle et al. |
| 2006/0020291 A1 | 1/2006 | Gozani et al. |
| 2006/0129205 A1 | 6/2006 | Boveja et al. |
| 2006/0135998 A1 | 6/2006 | Libbus et al. |
| 2006/0195159 A1 | 8/2006 | Bradley et al. |
| 2006/0212089 A1 | 9/2006 | Tass |
| 2006/0217782 A1 | 9/2006 | Boveja et al. |
| 2006/0264752 A1 | 11/2006 | Rubinsky et al. |
| 2006/0276722 A1 | 12/2006 | Litvak et al. |
| 2006/0287609 A1 | 12/2006 | Litvak et al. |
| 2007/0021800 A1 | 1/2007 | Bradley et al. |
| 2007/0073354 A1 | 3/2007 | Knudson et al. |
| 2007/0100378 A1 | 5/2007 | Maschino |
| 2007/0178579 A1 | 8/2007 | Ross et al. |
| 2007/0185409 A1 | 8/2007 | Wu et al. |
| 2007/0208394 A1 | 9/2007 | King et al. |
| 2007/0225765 A1 | 9/2007 | King |
| 2007/0225767 A1 | 9/2007 | Daly et al. |
| 2007/0244410 A1 | 10/2007 | Fridman et al. |
| 2007/0250120 A1 | 10/2007 | Flach et al. |
| 2007/0255372 A1 | 11/2007 | Metzler et al. |
| 2007/0265489 A1 | 11/2007 | Borgerding et al. |
| 2007/0282217 A1 | 12/2007 | McGinnis et al. |
| 2007/0287931 A1 | 12/2007 | Dilorenzo |
| 2008/0021292 A1 | 1/2008 | Stypulkowski |
| 2008/0051647 A1 | 2/2008 | Wu et al. |
| 2008/0064947 A1 | 3/2008 | Heruth et al. |
| 2008/0077039 A1* | 3/2008 | Donnett .............. A61B 5/0006 600/544 |
| 2008/0077191 A1 | 3/2008 | Morrell |
| 2008/0097529 A1 | 4/2008 | Parramon et al. |
| 2008/0132964 A1 | 6/2008 | Cohen et al. |
| 2008/0147155 A1 | 6/2008 | Swoyer et al. |
| 2008/0183076 A1 | 7/2008 | Witte et al. |
| 2008/0208304 A1 | 8/2008 | Zdravkovic et al. |
| 2008/0234780 A1 | 9/2008 | Smith et al. |
| 2008/0275527 A1 | 11/2008 | Greenberg et al. |
| 2008/0294221 A1 | 11/2008 | Kilgore |
| 2008/0300655 A1 | 12/2008 | Cholette |
| 2008/0319508 A1 | 12/2008 | Botros et al. |
| 2009/0030337 A1 | 1/2009 | Gozani et al. |
| 2009/0033486 A1 | 2/2009 | Costantino et al. |
| 2009/0058635 A1 | 3/2009 | Lalonde et al. |
| 2009/0082691 A1 | 3/2009 | Denison et al. |
| 2009/0149912 A1 | 6/2009 | Dacey, Jr. et al. |
| 2009/0157155 A1 | 6/2009 | Bradley |
| 2009/0270957 A1 | 10/2009 | Pianca |
| 2009/0281594 A1 | 11/2009 | Wacnik et al. |
| 2009/0287277 A1 | 11/2009 | Conn et al. |
| 2009/0299214 A1 | 12/2009 | Wu et al. |
| 2009/0306491 A1 | 12/2009 | Haggers |
| 2009/0306533 A1 | 12/2009 | Rousche et al. |
| 2010/0010388 A1 | 1/2010 | Panken et al. |
| 2010/0057159 A1 | 3/2010 | Lozano |
| 2010/0058126 A1 | 3/2010 | Chang et al. |
| 2010/0069835 A1 | 3/2010 | Parker et al. |
| 2010/0069996 A1 | 3/2010 | Strahl |
| 2010/0070007 A1 | 3/2010 | Parker et al. |
| 2010/0070008 A1 | 3/2010 | Parker et al. |
| 2010/0100153 A1 | 4/2010 | Carlson et al. |
| 2010/0106231 A1 | 4/2010 | Torgerson |
| 2010/0114237 A1 | 5/2010 | Giftakis et al. |
| 2010/0114258 A1 | 5/2010 | Donofrio et al. |
| 2010/0125313 A1 | 5/2010 | Lee et al. |
| 2010/0125314 A1 | 5/2010 | Bradley et al. |
| 2010/0145222 A1 | 6/2010 | Brunnett et al. |
| 2010/0152808 A1 | 6/2010 | Boggs |
| 2010/0179626 A1 | 7/2010 | Pilarski |
| 2010/0191307 A1 | 7/2010 | Fang et al. |
| 2010/0204748 A1 | 8/2010 | Lozano et al. |
| 2010/0222844 A1 | 9/2010 | Troosters et al. |
| 2010/0222858 A1 | 9/2010 | Meloy |
| 2010/0249643 A1 | 9/2010 | Gozani et al. |
| 2010/0249867 A1 | 9/2010 | Wanasek |
| 2010/0258342 A1 | 10/2010 | Parker |
| 2010/0262208 A1 | 10/2010 | Parker |
| 2010/0262214 A1 | 10/2010 | Robinson |
| 2010/0280570 A1 | 11/2010 | Sturm et al. |
| 2010/0286748 A1 | 11/2010 | Midani et al. |
| 2010/0331604 A1 | 12/2010 | Okamoto et al. |
| 2010/0331926 A1 | 12/2010 | Lee et al. |
| 2011/0004207 A1 | 1/2011 | Wallace et al. |
| 2011/0021943 A1 | 1/2011 | Lacour et al. |
| 2011/0028859 A1 | 2/2011 | Chian |
| 2011/0040546 A1 | 2/2011 | Gerber et al. |
| 2011/0077712 A1 | 3/2011 | Killian |
| 2011/0087085 A1 | 4/2011 | Tsampazis et al. |
| 2011/0093042 A1 | 4/2011 | Torgerson et al. |
| 2011/0106100 A1 | 5/2011 | Bischoff |
| 2011/0130802 A1 | 6/2011 | Libbus et al. |
| 2011/0184488 A1 | 7/2011 | De Ridder et al. |
| 2011/0204811 A1 | 8/2011 | Pollmann-retsch |
| 2011/0224665 A1 | 9/2011 | Crosby et al. |
| 2011/0224749 A1 | 9/2011 | Ben-David et al. |
| 2011/0264165 A1 | 10/2011 | Molnar et al. |
| 2011/0270343 A1 | 11/2011 | Buschman et al. |
| 2011/0288391 A1 | 11/2011 | Rao et al. |
| 2011/0307030 A1 | 12/2011 | John |
| 2011/0313310 A1 | 12/2011 | Tomita |
| 2011/0313483 A1 | 12/2011 | Hincapie et al. |
| 2012/0029377 A1 | 2/2012 | Polak |
| 2012/0059275 A1 | 3/2012 | Fagin et al. |
| 2012/0101552 A1 | 4/2012 | Lazarewicz et al. |
| 2012/0101826 A1 | 4/2012 | Visser et al. |
| 2012/0109004 A1 | 5/2012 | Cadwell |
| 2012/0109236 A1 | 5/2012 | Jacobson et al. |
| 2012/0155183 A1 | 6/2012 | Aritome |
| 2012/0185020 A1 | 7/2012 | Simon et al. |
| 2012/0245481 A1 | 9/2012 | Blanco et al. |
| 2012/0253423 A1 | 10/2012 | Youn et al. |
| 2012/0277621 A1 | 11/2012 | Gerber et al. |
| 2012/0277823 A1 | 11/2012 | Gerber et al. |
| 2012/0310301 A1 | 12/2012 | Bennett et al. |
| 2013/0041449 A1 | 2/2013 | Cela et al. |
| 2013/0053722 A1 | 2/2013 | Carlson et al. |
| 2013/0060302 A1 | 3/2013 | Polefko et al. |
| 2013/0172774 A1 | 7/2013 | Crowder et al. |
| 2013/0289661 A1 | 10/2013 | Griffith et al. |
| 2013/0289683 A1 | 10/2013 | Parker et al. |
| 2014/0046407 A1 | 2/2014 | Ben-ezra et al. |
| 2014/0066803 A1 | 3/2014 | Choi |
| 2014/0142447 A1 | 5/2014 | Takahashi et al. |
| 2014/0194771 A1 | 7/2014 | Parker et al. |
| 2014/0194772 A1 | 7/2014 | Single et al. |
| 2014/0236042 A1 | 8/2014 | Parker et al. |
| 2014/0236257 A1 | 8/2014 | Parker et al. |
| 2014/0243926 A1 | 8/2014 | Carcieri |
| 2014/0243931 A1 | 8/2014 | Parker et al. |
| 2014/0249396 A1 | 9/2014 | Shacham-diamand et al. |
| 2014/0276195 A1 | 9/2014 | Papay et al. |
| 2014/0277250 A1 | 9/2014 | Su et al. |
| 2014/0277267 A1 | 9/2014 | Vansickle et al. |
| 2014/0288551 A1 | 9/2014 | Bharmi et al. |
| 2014/0288577 A1 | 9/2014 | Robinson et al. |
| 2014/0296737 A1 | 10/2014 | Parker et al. |
| 2014/0324118 A1 | 10/2014 | Simon et al. |
| 2014/0350634 A1 | 11/2014 | Grill et al. |
| 2014/0358024 A1 | 12/2014 | Nelson et al. |
| 2015/0018699 A1 | 1/2015 | Zeng et al. |
| 2015/0025597 A1 | 1/2015 | Surth et al. |
| 2015/0032181 A1 | 1/2015 | Baynham et al. |
| 2015/0051637 A1 | 2/2015 | Osorio |
| 2015/0126839 A1 | 5/2015 | Li et al. |
| 2015/0148869 A1 | 5/2015 | Dorvall et al. |
| 2015/0164354 A1 | 6/2015 | Parker et al. |
| 2015/0174396 A1 | 6/2015 | Fisher et al. |

(56) References Cited

U.S. PATENT DOCUMENTS

| | | |
|---|---|---|
| 2015/0238104 A1 | 8/2015 | Tass |
| 2015/0238304 A1 | 8/2015 | Lamraoui |
| 2015/0282725 A1 | 10/2015 | Single |
| 2015/0313487 A1 | 11/2015 | Single |
| 2015/0360031 A1 | 12/2015 | Bornzin et al. |
| 2015/0374999 A1 | 12/2015 | Parker |
| 2016/0082265 A1 | 3/2016 | Moffitt et al. |
| 2016/0082268 A1 | 3/2016 | Hershey et al. |
| 2016/0101289 A1 | 4/2016 | Stolen et al. |
| 2016/0106980 A1 | 4/2016 | Sürth et al. |
| 2016/0121124 A1 | 5/2016 | Johanek et al. |
| 2016/0129272 A1 | 5/2016 | Hou et al. |
| 2016/0144189 A1 | 5/2016 | Bakker et al. |
| 2016/0166164 A1 | 6/2016 | Obradovic et al. |
| 2016/0175594 A1 | 6/2016 | Min et al. |
| 2016/0287126 A1 | 10/2016 | Parker et al. |
| 2016/0287182 A1 | 10/2016 | Single |
| 2016/0367808 A9 | 12/2016 | Simon et al. |
| 2017/0001017 A9 | 1/2017 | Parker et al. |
| 2017/0049345 A1 | 2/2017 | Single |
| 2017/0071490 A1 | 3/2017 | Parker et al. |
| 2017/0135624 A1 | 5/2017 | Parker |
| 2017/0157410 A1 | 6/2017 | Moffitt et al. |
| 2017/0173326 A1 | 6/2017 | Bloch et al. |
| 2017/0173335 A1 | 6/2017 | Min et al. |
| 2017/0173341 A1 | 6/2017 | Johanek et al. |
| 2017/0216587 A1 | 8/2017 | Parker |
| 2017/0361101 A1 | 12/2017 | Single |
| 2018/0071513 A1 | 3/2018 | Weiss et al. |
| 2018/0104493 A1 | 4/2018 | Doan et al. |
| 2018/0110987 A1 | 4/2018 | Parker |
| 2018/0117335 A1 | 5/2018 | Parker et al. |
| 2018/0132747 A1 | 5/2018 | Parker et al. |
| 2018/0132760 A1 | 5/2018 | Parker |
| 2018/0133459 A1 | 5/2018 | Parker et al. |
| 2018/0228391 A1 | 8/2018 | Parker et al. |
| 2018/0228547 A1 | 8/2018 | Parker |
| 2018/0229046 A1 | 8/2018 | Parker et al. |
| 2018/0256052 A1 | 9/2018 | Parker et al. |
| 2019/0001139 A1 | 1/2019 | Mishra et al. |
| 2019/0030339 A1 | 1/2019 | Baru et al. |
| 2019/0125269 A1 | 5/2019 | Markovic et al. |
| 2019/0168000 A1 | 6/2019 | Laird-wah |
| 2019/0216343 A1 | 7/2019 | Single et al. |
| 2019/0239768 A1 | 8/2019 | Karantonis et al. |
| 2019/0307341 A1 | 10/2019 | Parker et al. |
| 2019/0357788 A1 | 11/2019 | Single |
| 2020/0029914 A1 | 1/2020 | Single |
| 2020/0129108 A1 | 4/2020 | Parker et al. |
| 2020/0155240 A1 | 5/2020 | Parker et al. |
| 2020/0215331 A1 | 7/2020 | Single |
| 2020/0282208 A1 | 9/2020 | Parker |
| 2021/0001133 A1 | 1/2021 | Williams et al. |
| 2021/0008373 A1 | 1/2021 | Single et al. |
| 2021/0016091 A1 | 1/2021 | Parker et al. |
| 2021/0121696 A1 | 4/2021 | Parker et al. |
| 2021/0162214 A1 | 6/2021 | Parker |
| 2021/0267518 A1 | 9/2021 | Parker et al. |
| 2021/0308449 A1 | 10/2021 | Parker |
| 2021/0315502 A1 | 10/2021 | Parker et al. |
| 2021/0379386 A1 | 12/2021 | Parker et al. |
| 2021/0387005 A1 | 12/2021 | Parker et al. |
| 2021/0387008 A1 | 12/2021 | Single |
| 2021/0393964 A1 | 12/2021 | Single et al. |
| 2022/0007987 A1 | 1/2022 | Huang et al. |
| 2022/0039724 A1 | 2/2022 | Parker et al. |
| 2022/0151535 A1 | 5/2022 | Parker et al. |
| 2022/0151536 A1 | 5/2022 | Karantonis et al. |
| 2022/0168574 A1 | 6/2022 | Wah |
| 2022/0249009 A1 | 8/2022 | Parker et al. |

FOREIGN PATENT DOCUMENTS

| | | |
|---|---|---|
| CN | 103654762 A | 3/2014 |
| CN | 103842022 A | 6/2014 |
| CN | 104411360 A | 3/2015 |
| EP | 0219084 A2 | 4/1987 |
| EP | 1244496 A1 | 10/2002 |
| EP | 0998958 B1 | 8/2005 |
| EP | 2019716 A | 11/2007 |
| EP | 2243510 A2 | 10/2010 |
| EP | 2443995 A2 | 4/2012 |
| EP | 2520327 A2 | 11/2012 |
| EP | 2707095 A1 | 3/2014 |
| EP | 3229893 A1 | 10/2017 |
| JP | 2006504494 A | 2/2006 |
| JP | 2009512505 A | 3/2009 |
| JP | 2012524629 | 10/2012 |
| JP | 2013500779 A | 1/2013 |
| JP | 2013527784 A | 7/2013 |
| JP | 2013536044 A | 9/2013 |
| JP | 2014522261 A | 9/2014 |
| JP | 2014523261 A | 9/2014 |
| WO | 1983003191 A | 9/1983 |
| WO | 1993001863 A1 | 2/1993 |
| WO | 1996012383 A1 | 4/1996 |
| WO | 2000002623 A1 | 1/2000 |
| WO | 2002036003 A1 | 11/2001 |
| WO | 2002038031 | 5/2002 |
| WO | 2002049500 A2 | 6/2002 |
| WO | 2002082982 A1 | 10/2002 |
| WO | 2003028521 A2 | 4/2003 |
| WO | 2003043690 | 5/2003 |
| WO | 2003103484 A2 | 12/2003 |
| WO | 2004021885 A1 | 3/2004 |
| WO | 2004103455 | 12/2004 |
| WO | 2005032656 A1 | 4/2005 |
| WO | 2005105202 A1 | 11/2005 |
| WO | 2005122887 A2 | 12/2005 |
| WO | 2006091636 A2 | 8/2006 |
| WO | 2007050657 A1 | 5/2007 |
| WO | 2007064936 A1 | 6/2007 |
| WO | 2007127926 A2 | 11/2007 |
| WO | 2007130170 A1 | 11/2007 |
| WO | 2008004204 A1 | 1/2008 |
| WO | 2008049199 A1 | 5/2008 |
| WO | 2009002072 A2 | 12/2008 |
| WO | 2009002579 A1 | 12/2008 |
| WO | 2009001870 A2 | 1/2009 |
| WO | 2009130515 A2 | 10/2009 |
| WO | 2009146427 A1 | 12/2009 |
| WO | 2010013170 A1 | 2/2010 |
| WO | 2010044989 A2 | 4/2010 |
| WO | 2010051392 A1 | 5/2010 |
| WO | 2010051406 A1 | 5/2010 |
| WO | 2010057046 A2 | 5/2010 |
| WO | 2010124139 A1 | 10/2010 |
| WO | 2010138915 A1 | 12/2010 |
| WO | 2011011327 A1 | 1/2011 |
| WO | 2011014570 A1 | 2/2011 |
| WO | 2011017778 A1 | 2/2011 |
| WO | 2011066477 A1 | 6/2011 |
| WO | 2011066478 A1 | 6/2011 |
| WO | 2011112843 A1 | 9/2011 |
| WO | 2011119251 A2 | 9/2011 |
| WO | 2011159545 A2 | 12/2011 |
| WO | 2012016138 A1 | 2/2012 |
| WO | 2012027252 A2 | 3/2012 |
| WO | 2012027791 A1 | 3/2012 |
| WO | 2012155183 A1 | 11/2012 |
| WO | 2012155184 A1 | 11/2012 |
| WO | 2012155185 A1 | 11/2012 |
| WO | 2012155187 A1 | 11/2012 |
| WO | 2012155188 A1 | 11/2012 |
| WO | 2012155189 A1 | 11/2012 |
| WO | 2012155190 A1 | 11/2012 |
| WO | 2012162349 A1 | 11/2012 |
| WO | 2013063111 A1 | 5/2013 |
| WO | 2013075171 A1 | 5/2013 |
| WO | 2013116161 A1 | 8/2013 |
| WO | 2014071445 A1 | 5/2014 |
| WO | 2014071446 A1 | 5/2014 |
| WO | 2014143577 A1 | 9/2014 |
| WO | 2014150001 A1 | 9/2014 |

(56) References Cited

FOREIGN PATENT DOCUMENTS

| WO | 2015070281 A1 | 5/2015 |
|---|---|---|
| WO | 2015074121 A1 | 5/2015 |
| WO | 2015109239 A1 | 7/2015 |
| WO | 2015143509 A1 | 10/2015 |
| WO | 2015168735 A1 | 11/2015 |
| WO | 2016011512 A1 | 1/2016 |
| WO | 2016048974 A1 | 3/2016 |
| WO | 2016059556 A1 | 4/2016 |
| WO | 2016077882 A1 | 5/2016 |
| WO | 2016090420 A1 | 6/2016 |
| WO | 2016090436 A1 | 6/2016 |
| WO | 2016115596 A1 | 7/2016 |
| WO | 2016161484 A2 | 10/2016 |
| WO | 2016168798 A1 | 10/2016 |
| WO | 2016191807 A1 | 12/2016 |
| WO | 2016191808 A1 | 12/2016 |
| WO | 2016191815 A1 | 12/2016 |
| WO | 2017053504 A1 | 3/2017 |
| WO | 2017142948 A1 | 8/2017 |
| WO | 2017173493 A1 | 10/2017 |
| WO | 2017210352 A1 | 12/2017 |
| WO | 2017219096 A1 | 12/2017 |
| WO | 2018080753 A1 | 5/2018 |
| WO | 2018119220 A1 | 6/2018 |
| WO | 2018160992 A1 | 9/2018 |
| WO | 2018170141 A1 | 9/2018 |
| WO | 2019178634 A1 | 9/2019 |
| WO | 2019204884 A1 | 10/2019 |
| WO | 2019231796 A1 | 12/2019 |
| WO | 2020082118 A1 | 4/2020 |
| WO | 2020082126 A1 | 4/2020 |
| WO | 2020082128 A1 | 4/2020 |
| WO | 2020087123 A1 | 5/2020 |
| WO | 2020087135 A1 | 5/2020 |
| WO | 2020124135 A1 | 6/2020 |
| WO | 2021007615 A1 | 1/2021 |

OTHER PUBLICATIONS

Extended European Search Report for European Application 18910394.8 Search Completed Oct. 7, 2021, Mailed Oct. 15, 2021, 8 pgs.
Extended European Search Report for European Application 19876581.0 Search Completed Jun. 7, 2022, Mailed Jun. 15, 2022, 7 pgs.
Extended European Search Report for European Application No. 15789515.2, Search completed Dec. 4, 2017, Mailed Jan. 30, 2018, 7 Pgs.
Extended European Search Report for European Application No. 16802238.2, Search completed Oct. 17, 2018, Mailed Oct. 24, 2018, 8 Pgs.
Extended European Search Report for European Application No. 19793420.1, Search completed Dec. 6, 2021, Mailed Dec. 17, 2021, 9 Pgs.
Extended European Search Report for European Application No. 19875139.8, Search completed Jun. 7, 2022, Mailed Jun. 15, 2022, 8 Pgs.
Extended European Search Report for European Application No. 19899138.2, Search completed Jul. 26, 2022, Mailed Aug. 3, 2022, 09 Pgs.
International Search Report and Written Opinion for International Application No. PCT/AU2020/050725, Search completed Oct. 19, 2020, 8 Pgs.
Herreras, "Local Field Potentials: Myths and Misunderstandings", Frontiers in Neural Circuits, Dec. 15, 2016, vol. 10, Article 1101, 16 pgs., doi:10.3389/fncir.2016.00101.
Islam et al., "Methods for artifact detection and removal from scalp EEG: A review", Neurophysiologie Clinique—Clinical Neurophysiology, vol. 46, No. 4, pp. 287-305, XP029804850, DOI: 10.1016/J.NEUCLI.2016.07.002, 2016.
Kopelman et al., "Attempted Reversible Sympathetic Ganglion Block by An Implantable Neurostimulator", Interactive CardioVascular and Thoracic Surgery, Feb. 7, 2012, vol. 14, Issue 5, pp. 605-609, doi:10.1093/icvts/ivr137.

Li et al., "Therapeutic Deep Brain Stimulation in Parkinsonian Rats Directly Influences Motor Cortex", Neuron, vol. 76, No. 5, pp. 1030-1041, XP0289601 09, ISSN: 0896-6273, 001: 10.1 016/J.NEURON.2012.09.032, 2012.
Parker et al., "Electrically evoked compound action potential recording in peripheral nerves", Bioeletron. Med., vol. 1, No. 1, 2018, pp. 71-83.
Penar et al., "Cortical Evoked Potentials Used for Placement of a Laminotomy Lead Array: A Case Report", Neuromodulation: Technology at the Neural Interface, Apr. 19, 2011, doi: 10.1111/j.15251403.2011.00352.x.
Shepherd et al., "Electrical stimulation of the auditory nerve: II. Effect of stimulus waveshape on single fibre response properties", Hearing Research, 1999, 130, pp. 171-188.
Siegfried et al., "Bilateral Chronic Electrostimulation of Ventroposterolateral Pallidum: A New Therapeutic Approach for Alleviating all Parkinsonian Symptoms", Neurosurgery, 35, No. 6, Dec. 1994, pp. 1126-1130.
Tronnier et al., "Magnetic Resonance Imaging with Implanted Neurostimulators: An In Vitro and In Vivo Study", Jan. 1999, Neurosurgery, vol. 44(1), pp. 118-125 (Year: 1999).
Australian Examination Report for Application No. 2019283936, Mailed Apr. 1, 2021, 7 pages.
Extended European Search Report for EP Application 12785483.4 completed Sep. 16, 2014, 7 pgs.
Extended European Search Report for European Application 12785619.3 Search Completed Oct. 13, 2014, Mailed Oct. 23, 2014, 7 pgs.
Extended European Search Report for European Application 12785669.8 Search Completed Sep. 22, 2014, Mailed Sep. 29, 2014, 5 pgs.
Extended European Search Report for European Application No. 13852669.4, Search completed Jun. 8, 2016, Mailed Jun. 22, 2016, 09 Pgs.
Extended European Search Report for European Application No. 14861553.7, Search completed Jun. 8, 2017, Mailed Jun. 19, 2017, 8 Pgs.
Extended European Search Report for European Application No. 14863597.2, Search completed Jun. 6, 2017, Mailed Jun. 13, 2017, 9 Pgs.
Extended European Search Report for European Application No. 15768956.3, Search completed Oct. 3, 2017, Mailed Oct. 10, 2017, 8 Pgs.
Extended European Search Report for European Application No. 15861444.6, Search completed Jul. 13, 2018, Mailed Jul. 23, 2018, 8 pgs.
Extended European Search Report for European Application No. 16739680.3, Search completed Jun. 1, 2018, Mailed Jun. 12, 2018, 9 Pgs.
Extended European Search Report for European Application No. 16802237.4, Search completed Dec. 11, 2018, Mailed Dec. 19, 2018, 9 Pgs.
Extended European Search Report for European Application No. 17778477.4, report completed Nov. 12, 2019, mailed Nov. 20, 2019, 7 pgs.
Extended European Search Report for European Application No. 17814341.8, report completed Dec. 12, 2019, report mailed Jan. 2, 2020, 8 pgs.
Extended European Search Report for European Application No. 13853514.1, Search completed Jun. 8, 2016, Mailed Jun. 15, 2016, 07 Pgs.
International Preliminary Report for International Application No. PCT/AU2017/050296, Issued Oct. 9, 2018, 7 Pgs.
International Preliminary Report for International Application No. PCT/AU2017/050647, Issued Dec. 25, 2018, 8 pgs.
International Preliminary Report on Patentability for International Application No. PCT/AU2011/001127, Report Issued Mar. 5, 2013, 9 pgs.
International Preliminary Report on Patentability for International Application No. PCT/AU2012/000511, Report Issued Nov. 19, 2013, 6 pgs.
International Preliminary Report on Patentability for International Application No. PCT/AU2012/000512, Report Issued Nov. 19, 2013, 8 pgs.

(56) References Cited

OTHER PUBLICATIONS

International Preliminary Report on Patentability for International Application No. PCT/AU2012/000513, Report Issued Nov. 19, 2013, 11 pgs.
International Preliminary Report on Patentability for International Application No. PCT/AU2012/000515, Report Issued Nov. 19, 2013, 5 pgs.
International Preliminary Report on Patentability for International Application No. PCT/AU2012/000516, Report Issued Nov. 19, 2013, 9 pgs.
International Preliminary Report on Patentability for International Application No. PCT/AU2012/000517, Report Issued Nov. 19, 2013, 6 pgs.
International Preliminary Report on Patentability for International Application No. PCT/AU2012/000518, Report Issued Nov. 19, 2013, 11 pgs.
International Preliminary Report on Patentability for International Application No. PCT/AU2012/001441, Report Issued May 27, 2014, 10 pgs.
International Preliminary Report on Patentability for International Application No. PCT/AU2013/001279, Report Issued May 12, 2015, 6 pgs.
International Preliminary Report on Patentability for International Application No. PCT/AU2013/001280, Report Issued May 12, 2015, 6 pgs.
International Preliminary Report on Patentability for International Application No. PCT/AU2014/001049, Report Issued May 17, 2016, 5 pgs.
International Preliminary Report on Patentability for International Application No. PCT/AU2014/050369, Report Issued May 24, 2016, 8 pgs.
International Preliminary Report on Patentability for International Application No. PCT/AU2015/050135, Report Issued Oct. 4, 2016, 13 pgs.
International Preliminary Report on Patentability for International Application No. PCT/AU2015/050215, Report Issued Nov. 8, 2016, 4 pgs.
International Preliminary Report on Patentability for International Application No. PCT/AU2015/050422, Report Issued Jan. 31, 2017, 8 pgs.
International Preliminary Report on Patentability for International Application No. PCT/AU2015/050724, Report Issued May 23, 2017, 5 pgs.
International Preliminary Report on Patentability for International Application No. PCT/AU2015/050753, Report Issued Jun. 13, 2017, 7 pgs.
International Preliminary Report on Patentability for International Application No. PCT/AU2015/050787, Report Issued Jun. 13, 2017, 6 pgs.
International Preliminary Report on Patentability for International Application No. PCT/AU2016/050019, Report Issued Jul. 25, 2017, 9 pgs.
International Preliminary Report on Patentability for International Application No. PCT/AU2016/050263, Report Issued Oct. 10, 2017, 9 pgs.
International Preliminary Report on Patentability for International Application No. PCT/AU2018/050278, Issued Sep. 29, 2020, 7 pgs.
International Preliminary Report on Patentability for International Application No. PCT/AU2019/050384, Mailed Oct. 27, 2020, 8 pgs.
International Search Report & Written Opinion for International Application No. PCT/AU2013/001280, Search Completed Jan. 16, 2014, Mailed Jan. 16, 2014, 8 Pgs.
International Search Report & Written Opinion for International Application PCT/AU2013/001279, Search Completed Jan. 9, 2014, Mailed Jan. 9, 2014, 9 Pgs.
International Search Report and Written Opinion for International Application No. PCT/AU2011/001127, date completed Nov. 11, 2011, date mailed Nov. 15, 2011, 13 pgs.
International Search Report and Written Opinion for International Application No. PCT/AU2012/001441, International Filing Date Nov. 23, 2012, Search Completed Feb. 26, 2013, Mailed Feb. 26, 2013, 14 pgs.
International Search Report and Written Opinion for International Application No. PCT/AU2014/001049, Search completed Feb. 10, 2015, Mailed Feb. 10, 2015, 8 Pgs.
International Search Report and Written Opinion for International Application No. PCT/AU2014/050369, Search completed Feb. 20, 2015, Mailed Feb. 20, 2015, 14 Pgs.
International Search Report and Written Opinion for International Application No. PCT/AU2015/050135, Search completed Jun. 30, 2015, Mailed Jun. 30, 2015, 26 Pgs.
International Search Report and Written Opinion for International Application No. PCT/AU2015/050422, Search completed Oct. 14, 2015, Mailed Oct. 14, 2015, 17 Pgs.
International Search Report and Written Opinion for International Application No. PCT/AU2015/050724, Search completed May 9, 2016, Mailed May 9, 2016, 8 Pgs.
International Search Report and Written Opinion for International Application No. PCT/AU2015/050753, Search completed Feb. 10, 2016, Mailed Feb. 10, 2016, 10 Pgs.
International Search Report and Written Opinion for International Application No. PCT/AU2015/050787, Search completed Mar. 16, 2016, Mailed Mar. 16, 2016, 10 Pgs.
International Search Report and Written Opinion for International Application No. PCT/AU2016/050019, Search completed May 4, 2016, Mailed May 4, 2016, 16Pgs.
International Search Report and Written Opinion for International Application No. PCT/AU2016/050263, Search completed Nov. 16, 2016, Mailed Nov. 16, 2016, 8 Pgs.
International Search Report and Written Opinion for International Application No. PCT/AU2016/050430, Search completed Aug. 16, 2016, Mailed Aug. 16, 2016, 10 Pgs.
International Search Report and Written Opinion for International Application No. PCT/AU2016/050431, Search completed Aug. 16, 2016, Mailed Aug. 16, 2016, 11 Pgs.
International Search Report and Written Opinion for International Application No. PCT/AU2016/050439, Search completed Jul. 15, 2016, Mailed Jul. 15, 2016, 8 Pgs.
International Search Report and Written Opinion for International Application No. PCT/AU2017/050296, Search completed Jul. 28, 2017, Mailed Jul. 28, 2017, 10 Pgs.
International Search Report and Written Opinion for International Application No. PCT/AU2017/050647, Search completed Sep. 29, 2017, Mailed Sep. 29, 2017, 13 Pgs.
International Search Report and Written Opinion for International Application No. PCT/AU2018/050278, Search completed Jun. 18, 2018, Mailed Jun. 18, 2018, 12 Pgs.
International Search Report and Written Opinion for International Application No. PCT/AU2019/050384, Search completed Jun. 25, 2019, Mailed Jun. 25, 2019, 15 Pgs.
International Search Report and Written Opinion for International Application No. PCT/AU2019/051385, Search completed Mar. 24, 2020, Mailed Mar. 24, 2020, 8 Pgs.
International Search Report and Written Opinion for International Application No. PCT/AU2015/050215, Search completed Jul. 30, 2015, Mailed Jul. 30, 2015, 8 Pgs.
International Search Report for Australian Application 2011901829 Search Completed Feb. 6, 2012, Mailed Feb. 7, 2012, 3pgs.
International Search Report for International Application No. PCT/AU2012/000511, International Filing Date May 11, 2012, Search Completed May 17, 2012, Mailed May 18, 2012, 4 pgs.
International Search Report for International Application No. PCT/AU2012/000512, International Filing Date May 11, 2012, Search Completed Jul. 10, 2012, Mailed Jul. 11, 2012, 4 pgs.
International Search Report for International Application No. PCT/AU2012/000513, International Filing Date May 11, 2012, Search Completed May 29, 2012, Mailed May 30, 2012, 5 pgs.
International Search Report for International Application No. PCT/AU2012/000515, International Filing Date May 11, 2012, Search Completed May 21, 2012, Mailed Jun. 4, 2012, 5 pgs.

(56) References Cited

OTHER PUBLICATIONS

International Search Report for International Application No. PCT/AU2012/000516, International Filing Date May 11, 2012, Search Completed Jul. 11, 2012, Mailed Jul. 12, 2012, 8 pgs.
International Search Report for International Application No. PCT/AU2012/000517, International Filing Date May 11, 2012, Search Completed Jun. 4, 2012, Mailed Jun. 6, 2012, 3 pgs.
International Search Report for International Application No. PCT/AU2012/000518, International Filing Date May 11, 2012, Search Completed Jun. 8, 2012, Mailed Jun. 12, 2012, 4 pgs.
International Search Report for International Application No. PCT/AU2019/051151, International Filing Date Oct. 22, 2019, Search Completed Feb. 24, 2020, Mailed Feb. 24, 2020, 9 pgs.
International Search Report for International Application No. PCT/AU2019/051160, International Filing Date Oct. 23, 2019, Search Completed Jan. 28, 2020, Mailed Jan. 28, 2020, 13 pgs.
International Search Report for International Application No. PCT/AU2019/051163, International Filing Date Oct. 23, 2019, Search Completed Jan. 21, 2020, Mailed Jan. 31, 2020, 8 pgs.
International Search Report for International Application No. PCT/AU2019/051197, International Filing Date Oct. 30, 2019, Search Completed Jan. 21, 2020, Mailed Jan. 21, 2020, 15 pgs.
International Search Report for International Application No. PCT/AU2019/051210, International Filing Date Nov. 2, 2019, Search Completed Feb. 4, 2020, Mailed Feb. 4, 2020, 10 pgs.
International Type Search Report for International Application No. AU 2015902393, Search completed May 16, 2016, Mailed May 16, 2016, 8 Pgs.
Japanese Office Action for Application No. 2017-546830, Mailed Feb. 20, 2020, 5 pages with English translation.
Japanese Office Action for Application No. 2017-553090, Mailed Mar. 16, 2020, 12 pages with English translation.
Japanese Office Action for Application No. 2018-552138, Mailed Mar. 1, 2021, 7 pages with English translation.
Japanese Office Action for Application No. 2018-513699, Mailed Jun. 8, 2020, 7 pages with English translation.
Massachusetts Institute of Technology, The Compound Action Potential of the Frog Sciatic Nerve, Quantitative Physiology: Cells and Tissues. Fall, 1999, Retrieved from http://umech.mit.edu/freeman/6.021J/2001/lab.pdf on May 22, 2012.
Medtronic, Spinal Cord Stimulation, RestoreSensor Neurostimulator, Features and Specification: Specification, Printed Jun. 16, 2014, 2 pgs.
Medtronic, Spinal Cord Stimulation, RestoreSensor Neurostimulator, Features and Specification: Summary Printed Jun. 16, 2014, 1 pg.
Office Action for Chinese Patent Application No. 201680020725.4, dated Mar. 16, 2020, 8 pgs.
Partial European Search Report for European Application No. 16775966.1, Search completed Oct. 26, 2018, Mailed Nov. 6, 2018, 11 Pgs.
Supplementary European Search Report for European Application No. 11820923.8, report completed Dec. 9, 2013, report mailed Dec. 17, 2013, 6 pgs.
Written Opinion for International Application No. PCT/AU2012/000511, International Filing Date May 11, 2012, Search Completed May 17, 2012, Mailed May 18, 2012, 5 pgs.
Written Opinion for International Application No. PCT/AU2012/000512, International Filing Date May 11, 2012, Search Completed Jul. 10, 2012, Mailed Jul. 11, 2012, 7 pgs.
Written Opinion for International Application No. PCT/AU2012/000513, International Filing Date May 11, 2012, Search Completed May 29, 2012, Mailed May 30, 2012, 10 pgs.
Written Opinion for International Application No. PCT/AU2012/000515, International Filing Date May 11, 2012, Search Completed May 21, 2012, Mailed Jun. 4, 2012, 4 pgs.
Written Opinion for International Application No. PCT/AU2012/000516, International Filing Date May 11, 2012, Search Completed Jul. 11, 2012, Mailed Jul. 12, 2012, 8 pgs.
Written Opinion for International Application No. PCT/AU2012/000517, International Filing Date May 11, 2012, Search Completed Jun. 4, 2012, Mailed Jun. 6, 2012, 5 pgs.
Written Opinion for International Application No. PCT/AU2012/000518, International Filing Date May 11, 2012, Search Completed Jun. 8, 2012, Mailed Jun. 12, 2012, 10 pgs.
Medtronic, RestoreSensor Neurostimulator, Retrieved from: http://web.archive.org/web/20150328092923/http://professional.medtronic.com:80/pt/neuro/scs/prod/restore-sensor/features-specifications/index.html, Capture Date Jul. 9, 2012, Printed on May 11, 2017.
"Advanced Pain Therapy using Neurostimulation for Chronic Pain", Medtronic RestoreSensor clinical trial paper, Clinical summary, Nov. 2011, pp. 32.
"Battelle Neurotechnology—Moving Beyond The Limits In Neurotechnology", Battelle, www.battelle.org, May 2014, pp. 1-2.
"Evoke 12C Percutaneous Leads", Saluda Medical, specifications available in the "Evoke Surgical Guide", version 6, http://www.saludamedical.com/manuals/, retrieved May 2017.
"Haptic technology", Wikipedia, Retrieved from: http://en.wikipedia.org/wiki/Haptic_technology, Last modified on Sep. 15, 2014, Printed on Sep. 15, 2014, 5 pgs.
"Implants for surgery, Cardiac pacemakers", IS-1 standard ISO 5841-3-2000, Oct. 15, 2000.
"Neural Bypass Technology Enables Movement in Paralyzed Patient", Posted on Jul. 29, 2014, 6 a.m. in Brain chips/computer interface, pp. 1-2.
"Percutaneous Lead Kit", St. Jude Medical Clinician's Manual, Models 3143, 3146, 3149, 3153, 3156, 3159, 3183, 3186, 3189, published Sep. 2016, 24 pages.
"Spinal Cord Stimulation, About Spinal Cord Stimulation", Medtronic, Retrieved from: http://professional.medtronic.com/pt/neuro/scs/edu/about/index.htm, Printed on Jun. 16, 2014, 2 pgs.
"Wide bandwidth BioAmplifier", http://www.psylab.com/html/default_bioamp.htm, Printed Jan. 30, 2014, 1-3 pages.
Siegfried et al., "Bilateral Chronic Electrostimulation of Ventroposterolateral Pallidum: A New Therapeutic Approach for Alleviating All Parkinsonian Symptoms", Issue: vol. 35(6), Dec. 1994, p. 1126-1130.
Abrard et al., "A time-frequency blindsignal separation methodapplicable to underdetermined mixtures of dependent sources", Signal Processing 85 (2005) 1389-1403.
Alam et al., "Evaluation of optimal electrode configurations for epidural spinal cord stimulation in cervical spinal cord injured rats", Journal of Neuroscience Methods, Mar. 2015, 28 pgs.
Al-Ani et al., "Automatic removal of high-amplitude stimulus artefact from neuronal signal recorded in the subthalamic nucleus", Journal of Neuroscience Methods, vol. 198, Issue 1, 2011, pp. 135-146.
Andreassen et al., "Muscle Fibre Conduction Velocity in Motor Units of the Human Anterior Tibial Muscle: a New Size Principle Parameter", J. Physiol, (1987), 391, pp. 561-571.
Andy, "Parafascicular-Center Median Nuclei Stimulation for Intractable Pain and Dyskinesia (Painful-Dyskinesia)", Stereotactic and Functional Neurosurgery, Appl. Neurophysiol., 43, No. 3-5, 1980, pp. 133-144.
Bahmer et al., "Application of triphasic pulses with adjustable phase amplitude ratio (PAR) for cochlear ECAP recording: I. Amplitude growth functions", Journal of Neuroscience Methods, Clinical Neuroscience, 2012, vol. 205, pp. 202-211.
Bahmer et al., "Effects of electrical pulse polarity shape on intra cochlear neural responses in humans: Triphasic pulses with cathodic second phase", Hearing Research, 2013, vol. 306, pp. 123-130.
Balzer et al., "Localization of cervical and cervicomedullary stimulation leads for pain treatment using median nerve somatosensay evoked potential collision testing", Journal of Neurosurgery, Jan. 2011, vol. 114, No. 1: pp. 200-205.
Blum, "An Electronic System for Extracellular Neural Stimulation and Recording", Dissertation, Georgia Institute of Technology, Aug. 2007, Retrieved from http://smartech.gatech.edu/handle/1853/16192 on Jan. 30, 2012.
Borg et al., "Conduction velocity and refractory period of single motor nerve fibres in antecedent poliomyelitis", Journal of Neurology, Neurosurgery, and Psychiatry, vol. 50, 1987, 443-446.

(56) References Cited

OTHER PUBLICATIONS

Bratta et al., "Orderly Stimulation of Skeletal Muscle Motor Units with Tripolar Nerve Cuff Electrode", IEEE Transactions on Biomedical Engineering, vol. 36, No. 8, 1989, pp. 836-843.
Brown et al., "Impact of Deep Brain Stimulation on Upper Limb Askinesia in Parkinson's Disease", Annals of Neurology, 45, No. 4, 1999, pp. 473-488.
Casey et al., "Separation of Mixed Audio Sources by Independent Subspace Analysis", Mitsubishi Electric Research Laboratories (2001), 8 pgs.
Celestin et al., "Pretreatment Psychosocial Variables as Predictors of Outcomes Following Lumbar Surgery and Spinal Cord Stimulation: A Systematic Review and Literature Synthesis", American Academy of Pain Medicine, 2009, vol. 10, No. 4, pp. 639-653. doi:10.1111/j.1526-4637.2009.00632.X.
Cong et al., "A 32-channel modular bi-directional neural interface system with embedded DSP for closed-loop operation", 40th European Solid State Circuits Conference (ESSCIRC), 2014, pp. 99-102.
Connolly et al., "Towards a platform for prototyping control systems for optimization of neuromodulation therapies", IEEE Biomedical Circuits and Systems Conference (BioCAS), 2015, pp. 1-4.
Coquery et al., "Backward and forward masking in the perception of cutaneous stimuli", Perception & Psychophysics, 1973, vol. 13.No. 2, pp. 161-163.
Dawson, "The relative excitability and conduction velocity of sensory and motor nerve fibres in man", Journal of Physiology, 1956, vol. 131(2), pp. 436-451.
De Ridder et al., "Burst Spinal Cord Stimulation toward Paresthesia-Free Pain Suppression", Nuerosurgery-online.com, May 2010, vol. 66, No. 8, pp. 986-990.
Delgado et al., "Measurement and interpretation of electrokinetic phenomena", Pure Appl. Chem., 2005, vol. 77, No. 10, pp. 1753-1805.
Devergnas et al., "Cortical potentials evoked by deep brain stimulation in the subthalamic area", Frontiers in System Neuroscience, May 13, 2011, vol. 5, Article 30, 2011, doi:10.3389/fnsys.2011.00030.
Dijkstra, "Ultrasonic Distance Detection for a Closed-Loop Spinal Cord Stimulation System", Proceedings—19th International Conference—IEEE/EMBS Oct. 30-Nov. 2, 1997, Chicago, IL., 4 pgs.
Dillier et al., "Measurement of the electrically evoked compound action potential via a neural response telemetry system", Ann. Otol. Rhinol. Laryngol., May 2002, vol. 111, No. 5, pp. 407-414.
Doiron et al., "Persistent Na+ Current Modifies Burst Discharge By Regulating Conditional Backpropagation of Dendritic Spikes", Journal of Neurophysiology 89, No. 1 (Jan. 1, 2003): 324-337, doi:10.1152/jn.00729.2002.
England et al., "Increased Numbers of Sodium Channels Form Along Demyelinated Axons", Brain Research 548, No. 1-2 (May 10, 1991): 334-337.
Fagius, J et al., "Sympathetic Reflex Latencies and Conduction Velocities in Normal Man", Journal of Neurological Sciences, 1980. vol. 47, pp. 433-448.
Falowski et al., "Spinal Cord Stimulation: an update", Neurotherapeutics: The Journal of the American Society for Experimental Neuro Therapeutics 5, No. 1, Jan. 2008, pp. 86-99.
Fisher, "F-Waves—Physiology and Clinical Uses", TheScientificWorldJournal, (2007) 7, pp. 144-160.
Fitzpatrick et al., "A Nerve Cuff Design for the Selective Activation and Blocking of Myelinated Nerve Fibers", IEEE Engineering in Medicine and Biology Society, vol. 13, No. 2, 1991, pp. 906-907.
Franke et al., "An Online Spike Detection and Spike Classification Algorithm Capable of Instantaneous Resolution of Overlapping Spikes", Journal of Computational Neuroscience, 2010, vol. 29, No. 1-2, pp. 127-148.
French et al., "Information transmission at 500 bits/s by action potentials in a mechanosensory neuron of the cockroach", Neuroscience Letters, vol. 243, No. 1-3, Feb. 1, 1998, pp. 113-116.
Fuentes et al., "Spinal Cord Stimulation Restores Locomotion in Animal Models of Parkinson's Disease", Science, vol. 323, No. 5921, Mar. 20, 2009, pp. 1578-1582.
Gad et al., "Development of a multi-electrode array for spinal cord epidural stimulation to facilitate stepping and standing after a complete spinal cord injury in adult rats", Journal of NeuroEngineering and Rehabilitation 2013, 10:2, 18 pgs., http://www.jneuroengrehab.com/content/10/1/2.
George et al., "Vagus nerve stimulation: a new tool for brain research and therapy", Biological Psychiatry 47, No. 4, Feb. 15, 2000, pp. 287-295.
Gnadt et al., "Spectral Cancellation of Microstimulation Artifact for Simultaneous Neural Recording In Situ", IEEE Transactions on Biomedical Engineering, Oct. 2003, Date of Publication: Sep. 23, 2003, vol. 50, No. 10, pp. 1129-1135, DOI: 10.1109/TBME.2003.816077.
Goodall et al., "Modeling Study of Activation and Propagation delays During Stimulation of Peripheral Nerve Fibres with a Tripolar Cuff Electrode", IEEE Transactions on Rehabilitation Engineering, Sep. 1995, vol. 3, No. 3, pp. 272-282.
Gorman et al., "ECAP Mapping of the Spinal Cord: Influence of Electrode Position on Aβ Recruitment", (2012)., In 16th Annual Meeting. Presented at the North American Neuromodulation Society, Las Vegas, NV, 2 pgs.
Gorman et al., "Neural Recordings For Feedback Control Of Spinal Cord Stimulation: Reduction Of Paresthesia Variability.", 2013, In International Neuromodulation Society 11th World Congress, presented at the International Neuromodulation Society 11th World Congress, Berlin, Germany, 2 pgs.
Hallstrom et al, "Distribution of lumbar spinal evoked potentials and their correlation with stimulation-induced paresthesiae", Electroencephalography and Clinical Neurophysiology, Mar.-Apr. 1991, vol. 80, No. 2, pp. 126-139, doi:10.1016/0168-5597(91)90150-V.
Harper et al., "Conduction Velocity is Related to Morphological Cell Type in Rat Dorsal Root Ganglion Neurones", J. Physiol, (1985), vol. 359, pp. 31-46.
He et al., "Perception threshold and electrode position for spinal cord stimulation", Pain, vol. 59, (1994), pp. 55-63.
Holsheimer et al., "Optimum Electrode Geometry for Spinal Cord Stimulation: the Narrow Bipole and Tripole", Medical and Biological Engineering and Computing, 1997, vol. 35, No. 5, pp. 493-497.
Holsheimer et al., "Significance of the Spinal Cord Position in Spinal Cord Stimulation", Acta Neurochir (1995) [Suppl] 64, pp. 119-124.
Holsheimer et al., "Spinal Geometry and Paresthesia Coverage in Spinal Cord Stimulation", Neuromodulation, 1998, vol. 1, No. 3, pp. 129-136.
Howell et al., "Evaluation of Intradural Stimulation Efficiency and Selectivity in a Computational Model of Spinal Cord Stimulation", PLOS ONE, DOI: 10.1371/journal.pone.0114938, Dec. 23, 2014.
Huff, Terry B. et al., "Real-Time CARS Imaging Reveals a Calpain-Dependent Pathway for Paranodal Myelin Retraction during High-Frequency Stimulation", PLoS ONE, vol. 6, Issue 3 (Mar. 3, 2011): e17176, 11 pgs., doi:10.1371/journal.pone.0017176.
Jang et al, "Single Channel Signal Separation Using Time-Domain Basis Functions", IEEE Signal Processing Letters, Jun. 2003, vol. 10, No. 6, 13 pgs.
Jang et al., "A Maximum Likelihood Approach to Single-channel Source Separation", Journal of Machine Learning Research, Dec. 2003, vol. 4, pp. 1365-1392.
Jeffrey et al., "A reliable method for intracranial electrode implantation and chronic electrical stimulation in the mouse brain", BMC Neuroscience. Biomed Central. London, GB. vol. 14. No. 1, Aug. 6, 2013 (Aug. 6, 2013), pp. 1-8.
Jones et al., "Scaling of Electrode-Electrolyte Interface Model Parameters In Phosphate Buffered Saline", IEEE Transactions on Biomedical Circuits and Systems, 2015, vol. 9, No. 3, pp. 441-448, DOI: 10.1109/TBCAS.2014.4223759.
Kent, "Characterization of Evoked Potentials During Deep Brain Stimulation in the Thalamus", Dissertation, Duke University, 2013, Retrieved from https://hdl.handle.net/10161/8195. https://dukespace.lib.duke.edu/dspace/handle/10161/8195.

(56) References Cited

OTHER PUBLICATIONS

Kent et al., "Instrumentation to Record Evoked Potentials for Closed-Loop Control of Deep Brain Stimulation", Conf. Proc. IEEE Eng. Med Biol. Sol, Aug. 2012, pp. 6777-6780, doi:10.1109/IEMBS. 20113.6091671.

Kent et al., "Recording evoked potentials during deep brain stimulation: development and validation of instrumentation to suppress the stimulus artefact", J Neural Eng., Jun. 2012, vol. 9, No. 3, 036004, doi: 10.1088/17412560/9/3/036004.

Kim et al., "A Wavelet-Based Method for Action Potential Detection From Extracellular Neural Signal Recording With Low Signal-to-Noise Ratio", IEEE Transactions On Biomedical Engineering, Aug. 2003, vol. 50. No. 8, pp. 999-1011.

Kim et al., "Cell Type-specific Changes of the Membrane Properties of Peripherally-axotomized Dorsal Root Ganglion Neurons in a Rat Model of Neuropathic Pain", Neuroscience, vol. 86, No. 1, May 21, 1998, pp. 301-309, doi:10.1016/S0306-4522(98)00022-0.

Krames et al., "Neuromodulation", 1st Edition, Academic Press, 2009, pp. 540-541.

Krarup, "Compound sensory action potential in normal and pathological human nerves", Muscle & Nerve, Apr. 2004, vol. 29, No. 4, pp. 465-483.

Krishnan et al., "Excitability Differences in Lower-Limb Motor Axons During and After Ischemia", Muscle & nerve, vol. 31, No. 2 (2005), pp. 205-213.

Kumar et al., "Deep Brain Stimulation for Intractable Pain: a 15-year Experience", Neurosurgery, Issue 40, No. 4, Apr. 1997, pp. 736-747.

Kumar et al., "Double-blind evaluation of subthalamic nucleus deep brain stimulation in advanced Parkinson's disease", by the American Academy of Neurology, 51, No. 3, Sep. 1, 1998, pp. 850-855.

Kumar et al., "Globus Pallidus Deep Brain Stimulation for Generalized Dystonia: Clinical and PET Investigation", Sep. 11, 1999, vol. 53, No. 4, pp. 871-874, doi:10.1212/WNL.53.4.871.

Laird et al., "A Model of Evoked Potentials in Spinal Cord Stimulation", IEEE Engineering in Medicine & Biology Society, 35th Annual Conference. Osaka, Japan: Jul. 3-7, 2013, pp. 6555-6558.

Laird-Wah, "Improving Spinal Cord Stimulation: Model-Based Approaches to Evoked Response Telemetry", UNSW Thesis, Aug. 2015, 279 pgs.

Lempka, "The Electrode-Tissue Interface During Recording and Stimulation In The Central Nervous System", Thesis, 155 pgs., published May 2010.

Levy et al., "Incidence and Avoidance of Neurologic Complications with Paddle Type Spinal Cord Stimulation Leads", Neuromodulation, Sep. 2011, vol. 14, No. 15, pp. 412-422, https://doi.org/10.1111/j.1525-1403.2011.00395.x.

Li, S. et al., "Resonant antidromic cortical circuit activation as a consequence of high-frequency subthalamic deep-brain stimulation", J Neurophysiol. Dec. 2007; 98(6): 3525-37. First published Oct. 10, 2007. doi:10.1152/jn.00808.2007.

Ma et al., "Similar Electrophysiological Changes in Axotomized and Neighboring Intact Dorsal Root Ganglion Neurons", Journal of Neurophysiology 89, No. 3 (Mar. 1, 2003): 1588-1602, doi:10.1152/jn.00855.2002.

MacEfield, "Spontaneous and Evoked Ectopic Discharges Recorded from Single Human Axons", Muscle & Nerve 21, No. 4, Apr. 1998, pp. 461-468.

Madhukar et al., "Modelling of compound nerve action potentials health and disease", Engineering in Medicine and Biology Society, 1992 14th Annual International Conference of the IEEE. vol. 6. IEEE, 1992. pp. 2600-2601.

Mahnam et al., "Measurement of the current-distance relationship using a novel refractory interaction technique", J. Neural Eng. 6(2): 036005, published May 20, 2009, 22 pgs.

Mannan et al., "Identification and Removal of Physiological Artifacts From Electroencephalogram Signals: A Review", IEEE Access, May 31, 2018, vol. 6, pp. 30630-30652, https://doi.org/10.1109/ACCESS.2018.2842082.

Markandey, "ECG Implementation on the TMS320C5515 DSP Medical Development Kit (MDK)", Texas Instruments Application Report Jun. 2010, 35 pgs.

Matzner et al., "Na+ Conductance and the Threshold for Repetitive Neuronal Firing", Brain Research 597, No. 1 (Nov. 27, 1992): 92-98, doi:10.1016/0006-8993(92)91509-D.

McGill, et al., "On the Nature and Elimination of Stimulus Artifact in Nerve Signals Evoked and Recorded Using Surface Electrodes", IEEE Transactions On Biomedical Engineering, vol. BME-29, No. 2, Feb. 1982, pp. 129-137.

Melzack et al., "Pain mechanisms: a new theory", Science, New York, New York, vol. 150, No. 3699, Nov. 19, 1965, pp. 971-979.

Miles et al., "An Electrode for Prolonged Stimulation of the Brain", Proc. 8th Meeting World Soc. Stereotactic and Functional Neurosurgery, Part III, Zurich, 1981, Appl. Neurophysiol, 45, 1982, pp. 449-445.

Misawa et al., "Neuropathic Pain Is Associated with Increased Nodal Persistent Na(+) Currents in Human Diabetic Neuropathy", Journal of the Peripheral Nervous System: JPNS, 14, No. 4 (Dec. 2009): 279-284.

Niazy et al., "Removal of FMRI environment artifacts from EEG data using optimal basis sets", NeuroImage, 2005, vol. 28, pp. 720-737, available online Sep. 16, 2005, doi: 10.1016/j.neuroimage. 2005.06.0607.

Nordin et al., "Ectopic Sensory Discharges and Paresthesiae in Patients with Disorders of Peripheral Nerves, Dorsal Roots and Dorsal Columns", Pain 20, No. 3 (Nov. 1984): 231-245, doi:10. 1016/0304-3959(84)90013-7.

North et al., "Prognostic value of psychological testing in patients undergoing spinal cord stimulation: a prospective study", Neurosurgery, Aug. 1, 1996, vol. 39, Issue 2, pp. 301-311. https://doi.org/10.1097/00006123-199608000-00013.

Oakley et al., "Spinal Cord Stimulation: Mechanisms of Action", Spine 27, No. 22, Nov. 15, 2002, pp. 2574-2583.

Oakley et al., "Transverse Tripolar Spinal Cord Stimulation: Results of an International Multicenter Study", Neuromodulation, vol. 9, No. 3, 2006, pp. 192-203.

Obradovic et al., "Effect of pressure on the spinal cord during spinal cord stimulation in an animal model", Poster, 18th Annual Meeting of the North American Neuromodulation Society, Dec. 11-14, 2014, Las Vegas.

Oh et al., "Long-term hardware-related complications of deep brain stimulation", Neurosurgery, vol. 50, No. 6, Jun. 2002, pp. 1268-1274, discussion pp. 1274-1276.

Olin et al., "Postural Changes in Spinal Cord Stimulation Perceptual Thresholds", Neuromodulation, vol. 1, No. 4, 1998, pp. 171-175.

Opsommer, E. et al., "Determination of Nerve Conduction Velocity of C-fibres in Humans from Thermal Thresholds to Contact Heat (Thermode) and from Evoked Brain Potentials to Radiant Heat ($CO_2$ Laser)", Neurophysiologie Clinique 1999, vol. 29, pp. 411-422.

Orstavik et al., "Pathological C-fibres in patients with a chronic painful condition", Brain (2003), 126, 567-578.

Ouyang et al., "Compression Induces Acute Demyelination and Potassium Channel Exposure in Spinal Cord", Journal of Neurotrauma 27, No. 6, Jun. 2010, 1109-1120, doi:10.1089/neu.2010.1271.

Parker et al., "Closing the Loop in Neuromodulation Therapies: Spinal Cord Evoked Compound Action Potentials During Stimulation for Pain Management (230).", 2011, In 15th Annual Meeting, North American Neuromodulation Society (p. 48). Presented at the North American Neuromodulation Society, Las Vegas.

Parker et al., "Compound Action Potentials Recorded in the Human Spinal Cord During Neurostimulation for Pain Relief", Pain, vol. 153, 2012, pp. 593-601.

Parker et al., "Electrically Evoked Compound Action Potentials Recorded From the Sheep Spinal Cord", Neuromodulation, vol. 16, 2013, pp. 295-303.

Penar et al., "Cortical Evoked Potentials Used for Placement of a Laminotomy Lead Array: A Case Report", Neuromodulation: Technology at the Neural Interface, accessed Apr. 19, 2011, doi:10.1111/j.1525-1403.2011.00352.x.

(56) References Cited

OTHER PUBLICATIONS

Peterson et al., "Stimulation artifact rejection in closed-loop, distributed neural interfaces", ESSCIRC, 42nd European Solid-State Circuits Conference, Lausanne, 2016, pp. 233-235.
Rattay, "Analysis of Models for External Stimulation of Axons", IEEE Transactions on Biomedical Engineering, vol. BME-33, No. 10, Oct. 1986, pp. 974-977.
Richter et al., "EMG and SSEP Monitoring During Cervical Spinal Cord Stimulation", Journal of Neurosurgical Review 2011, Southern Academic Press, 1(S1), 2011, pp. 61-63.
Ridder et al., "Burst Spinal Cord Stimulation for Limb and Back Pain", World Neurosurgery, 2013, 9 pgs.
Rijkhoff et al., "Acute Animal Studies on the Use of Anodal Block to Reduce Urethral Resistance in Sacral Root Stimulation", IEEE Transactions on Rehabilitation Engineering, 1994, vol. 2, No. 2, pp. 92-99.
Rijkhoff et al., "Orderly Recruitment of Motoneurons in an Acute Rabbit Model", Annual International Conference of the IEEE Engineering in Medicine and Biology Society, 1998, vol. 20, No. 5, pp. 2564-2565.
Ross et al., "Improving Patient Experience with Spinal Cord Stimulation: Implications of Position-Related Changes in Neurostimulation", Neuromodulation 2011; e-pub ahead of print. DOI: 10.1111/j.1525-1403.2011.00407.x 6 pages.
Roy et al., "Effects of Electrode Location on Myoelectric Conduction Velocity and Median Frequency Estimates", J. Appl. Physiol. 61 (4), 1986, pp. 1510-1517.
Sayenko et al., "Neuromodulation of evoked muscle potentials induced by epidural spinal-cord stimulation in paralyzed individuals", Journal of Neurophysiology, vol. 111, No. 5, 2014, pp. 1088-1099, First published Dec. 11, 2013.
Schmidt et al., "Gating of tactile input from the hand", Exp Brain Res, 1990, 79, pp. 97-102.
Scott et al., "Compact Nonlinear Model of an Implantable Electrode Array for Spinal Cord Stimulation (SCS)", IEEE Transactions on Biomedical Circuits and Systems, 2014, vol. 8, No. 3, pp. 382-390.
Siegfried et al., "Intracerebral Electrode Implantation System", Journal of Neurosurgery, vol. 59, No. 2, Aug. 1983, pp. 356-359.
Srinivasan, "Electrode/Electrolyte Interfaces: Structure and Kinetics of Charge Transfer", Fuel Cells, 2006, Chapter 2, 67 Pages.
Stanslaski et al., "Design and Validation of a Fully Implantable, Chronic, Closed-Loop Neuromodulation Device With Concurrent Sensing and Stimulation", IEEE Transactions on Neural Systems and Rehabilitation Engineering, Jul. 2012, Date of Publication: Jan. 23, 2012, vol. 20, No. 4, pp. 410-421, DOI: 10.1109/TNSRE.2012.2183617.
Struijk, "The Extracellular Potential of a Myelinated Nerve Fiber in an Unbounded Medium and in Nerve Cuff Models", Biophysical Journal vol. 72 Jun. 1997, 2457-2469.
Struijk et al, "Paresthesia Thresholds in Spinal Cord Stimulation: A Comparison of Theoretical Results with Clinical Data", IEEE Transactions on Rehabilitation Engineering, vol. 1, No. 2, Jun. 1993, pp. 101-108.
Struijk et al., "Excitation of Dorsal Root Fibers in Spinal Cord Stimulation: a Theoretical Study", IEEE Transactions on Biomedical Engineering, Jul. 1993, vol. 40, No. 7, pp. 632-639.
Sufka et al., "Gate Control Theory Reconsidered", Brain and Mind, 3, No. 2, 2002, pp. 277-290.
Takahashi et al, "Classification of neuronal activities from tetrode recordings using independent component analysis", Neurocomputing, (2002), vol. 49, Issues 1-4, pp. 289-298.
Tamura et al., "Increased Nodal Persistent Na+ Currents in Human Neuropathy and Motor Neuron Disease Estimated by Latent Addition", Clinical Neurophysiology 117, No. 11 (Nov. 2006): 2451-2458, doi: 10.1016/j.clinph.2006.07.309.
Tasker, "Deep Brain Stimulation is Preferable to Thalamotomy for Tremor Suppression", Surgical Neurology, 49, No. 2, 1998, pp. 145-153.
Taylor et al., "Spinal Cord Stimulation for Chronic Back and Leg Pain and Failed Back Surgery Syndrome: A Systematic Review and Analysis of Prognostic Factors", SPINE, vol. 30, No. 1, 2004, pp. 152-160.
Texas Instruments, "Precision, Low Power Instrumentation Amplifiers", Texas Instruments SBOS051B Oct. 1995, Revised Feb. 2005, 20 pgs.
Tomas et al., "Dorsal Root Entry Zone (DREZ) Localization Using Direct Spinal Cord Stimulation Can Improve Results of the DREZ Thermocoagulation Procedure for Intractable Pain Relief", Pain, 2005, vol. 116, pp. 159-163.
Tscherter et al., "Spatiotemporal Characterization of Rhythmic Activity in Rat Spinal Cord Slice Cultures", European Journal of Neuroscience 14, No. 2 (2001), pp. 179-190.
Van Den Berg et al., "Nerve fiber size-related block of action currents by phenytoin in mammalian nerve", Epilepsia, Nov. 1994, 35(6), pp. 1279-1288.
Villavicencio, Alan T. "Laminectomy versus Percutaneous Electrode Placement for Spinal Cord Stimulation," Neurosurgery, vol. 46 (2), Feb. 2000, pp. 399-405.
Vleggeert et al., "Electrophysiology and morphometry of the Aalpha- and Abeta-fiber populations in the normal and regenerating rat sciatic nerve", Experimental Neurology, vol. 187, No. 2, Jun. 1, 2004, Available online Apr. 2, 2004, pp. 337-349.
Woessner, "Blocking Out the Pain, Electric Nerve Block Treatments for Sciatic Neuritis", Retrieved from: http://www.practicalpainmanagement.com/pain/spine/radiculopathy/blocking-out-pain, Last updated Jan. 10, 2012.
Wolter et al., "Effects of sub-perception threshold spinal cord stimulation in neuropathic pain: A randomized controlled double-blind crossover study", European Federation of International Association for the Study of Pain Chapters, 2012, pp. 648-655.
Wu et al., "Changes in Aβ Non-nociceptive Primary Sensory Neurons in a Rat Model of Osteoarthritis Pain", Molecular Pain 6, No. 1 (Jul. 1, 2010): 37, doi:10.1186/1744-8069-6-37.
Xie et al., "Functional Changes in Dorsal Root Ganglion Cells after Chronic Nerve Constriction in the Rat", Journal of Neurophysiology 73, No. 5 (May 1, 1995): 1811-1820.
Xie et al., "Sinusoidal Time-Frequency Wavelet Family and its Application in Electrograstrographic Signal Analysis", Proceedings of the 20th Annual International Conference of the IEEE Engineering in Medicine and Biology Society, vol. 20, No. 3, Oct. 29, 1998, pp. 1450-1453.
Yamada et al., "Extraction and Analysis of the Single Motor Unit F-Wave of the Median Nerve", EMG Methods for Evaluating Muscle and Nerve Function, InTech, 2012, 15 pgs.
Yearwood, "Pulse Width Programming in Spinal Cord Stimulation: a Clinical Study", Pain Physician. 2010. vol. 13, pp. 321-335.
Yingling et al., "Use of Antidromic Evoked Potentials in Placement of Dorsal Cord Disc Electrodes", Applied Neurophysiology, 1986, vol. 49, pp. 36-41.
Yuan et al., "Recording monophasic action potentials using a platinum-electrode ablation catheter", Europace. Oct. 2000; 2(4):312-319.
Zhang et al., "Automatic Artifact Removal from Electroencephalogram Data Based on A Priori Artifact Information", BioMed Research International, Aug. 25, 2015, Article ID 720450, 8 pgs., DOI: https://doi.org/10.1155/2015/720450.
Zhou et al., "A High Input Impedance Low Noise Integrated Front-End Amplifier for Neural Monitoring", IEEE Transactions on Biomedical Circuits and Systems, 2016, vol. 10, No. 6, pp. 1079-1086.

\* cited by examiner

ASSESSING NEURAL STATE FROM ACTION POTENTIALS

CROSS-REFERENCE TO RELATED APPLICATIONS

This application is a continuation of U.S. patent application Ser. No. 15/129,407 entitled "Assessing Neural State from Action Potentials", filed Sep. 26, 2016 which is a national stage of PCT Application No. PCT/AU2015/050135 filed Mar. 27, 2015 which claims the benefit of Australian Provisional Patent Application No. 2014901110 filed Mar. 28, 2014, the disclosures of which are incorporated herein by reference in their entireties.

TECHNICAL FIELD

The present invention relates to assessing a neural state from neural potentials, and in particular relates to obtaining a recording of a neural potential arising on neural tissue, and monitoring for an anomalous profile of the recording, in order to assess the existence, state or progress of a neural disease.

BACKGROUND OF THE INVENTION

Neuropathic pain arises from damage or disease affecting the somatosensory system, and may result from disorders of the peripheral nervous system or the central nervous system. For example, complex regional pain syndrome (CRPS) is a severe type of pain disorder.

There is no known single pathognomonic symptom or sign of neuropathic disease. Consequently, it is difficult to diagnose neuropathic disease and to monitor the progress of neuropathic disease. No conclusive objective diagnostic exists for neuropathic pain, and clinicians must rely largely on a subjective clinical observation of the patient's responses. Neuropathic pain is also difficult to treat and often responds poorly to standard pain treatments.

A range of medications for treating neuropathic pain exist, including gabapentin for example. Careful documentation and appropriate monitoring of treatment are important for the safe and effective use of such medications, however this is difficult to achieve due to the difficulty of determining the disease state or monitoring the progress of the disease or symptoms. Advanced therapies for treating neuropathic pain include spinal cord stimulation.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In this specification, a statement that an element may be "at least one of" a list of options is to be understood that the element may be any one of the listed options, or may be any combination of two or more of the listed options.

SUMMARY OF THE INVENTION

According to a first aspect the present invention provides a method of assessing a neural state of a subject, the method comprising:
    obtaining a recording of a compound action potential arising in neural tissue of the subject;
    processing the recording to determine whether a profile of the recorded compound action potential is anomalous; and
    outputting an indication regarding the neural state of the subject based on determined anomalies in the recorded compound action potential.

A method for determining whether a human patient has neuropathic disease, comprising:
    obtaining a recording of a compound action potential arising in neural tissue of the patient; and
    diagnosing the patient as having neuropathic disease if a profile of the recorded compound action potential is anomalous.

A non-transitory computer readable medium for assessing a neural state of a subject, comprising instructions which, when executed by one or more processors, causes performance of the following:
    obtaining a recording of a compound action potential arising in neural tissue of the subject;
    processing the recording to determine whether a profile of the recorded compound action potential is anomalous; and
    outputting an indication regarding the neural state of the subject based on determined anomalies in the recorded compound action potential.

The detection of irregularities or anomalies in the recorded response may comprise any one or more of:
    determining whether more than three peaks exist in the recorded compound action potential;
    determining whether a peak in the recorded compound action potential is unexpectedly broad;
    determining whether a peak in the recorded compound action potential has an atypically swift rate of rise;
    determining whether anomalous frequency components exist in the recorded compound action potential when assessed in the frequency domain;
    determining a degree of deviation of the recorded compound action potential from a predefined expected response profile and, if the degree of deviation exceeds a predetermined threshold, indicating that the recorded response is anomalous.

Some embodiments may determine whether more than three peaks exist in the recorded compound action potential by measuring an amplitude or power of the recorded compound action potential in a time window positioned after cessation of a normal response. The amplitude or power of the recorded compound action potential in such a time window can be used to assess the presence or absence of an abnormal response arising later than a normal P2 peak. Additionally or alternatively, a matched filter or other signal processing means may be used to detect the presence of an extra lobe in the recorded compound action potential.

Some embodiments of the present invention thus recognise that when considering a recorded compound action potential (CAP) obtained from a person suffering from an altered neural state such as CRPS, rather than the CAP taking a typical three lobed profile, lobe deformation or additional lobes referred to herein as doublets can be observed to arise in the ECAP. Moreover, the degree of lobe deformation and/or the relative size of the additional lobes appearing in the response can he measured, in order to give not only a binary diagnosis but also a quantitative measure of the severity of the disease suffered by the person. Absence of such response profile anomalies may be used to eliminate some diseases from a diagnosis for the person. Repeated assessment of the recorded response profile from time to time, for example throughout administration of a therapy, may be used to assess disease state, disease progress, and therapy efficacy, and may be used to guide therapy modifications and optimisation over time. Therapy modifications may include modifications of dosage of a medicament and/or modification of a stimulus regime applied by a spinal column stimulator.

Accordingly, the present invention recognises that monitoring for the occurrence and severity of anomalies such as doublets in the recorded response profile gives a diagnostic for neuropathic pain or neural damage or in general any neural disease which gives rise to atypical neural response profiles.

Notably, some embodiments of the present invention further recognise that when application of a stimulus to a first neural site gives rise to anomalies in a recorded neural response profile, application of the same stimulus to an alternative neural site might give rise to a recorded neural response without abnormalities. Such embodiments may thus provide for identifying a locus of neuropathic pain.

The method of the present invention may in some embodiments be performed intra-operatively for example to effect electrode array implantation site optimisation. The method of the present invention may additionally or alternatively be performed during an implant programming stage in order to optimise electrode selection to a site at which a locus of neuropathic pain is identified.

The invention may further provide for intra-operative monitoring of the response profile during a sympathectomy procedure, in order to provide an intra-operative progressive indication of efficacy of the sympathectomy.

According to a further aspect the present invention provides a method of treating a neural disease, the method comprising:
  ordering or requesting the result of the method of the first aspect; and
  administering or modifying a therapy in a manner responsive to the ordered result.

The compound action potential may arise from deliberate stimulation, whether peripheral stimulation or direct spinal column stimulation, for example.

BRIEF DESCRIPTION OF THE DRAWINGS

An example of the invention will now be described with reference to the accompanying drawings, in which.

DESCRIPTION OF THE PREFERRED EMBODIMENTS

Figure 1A:
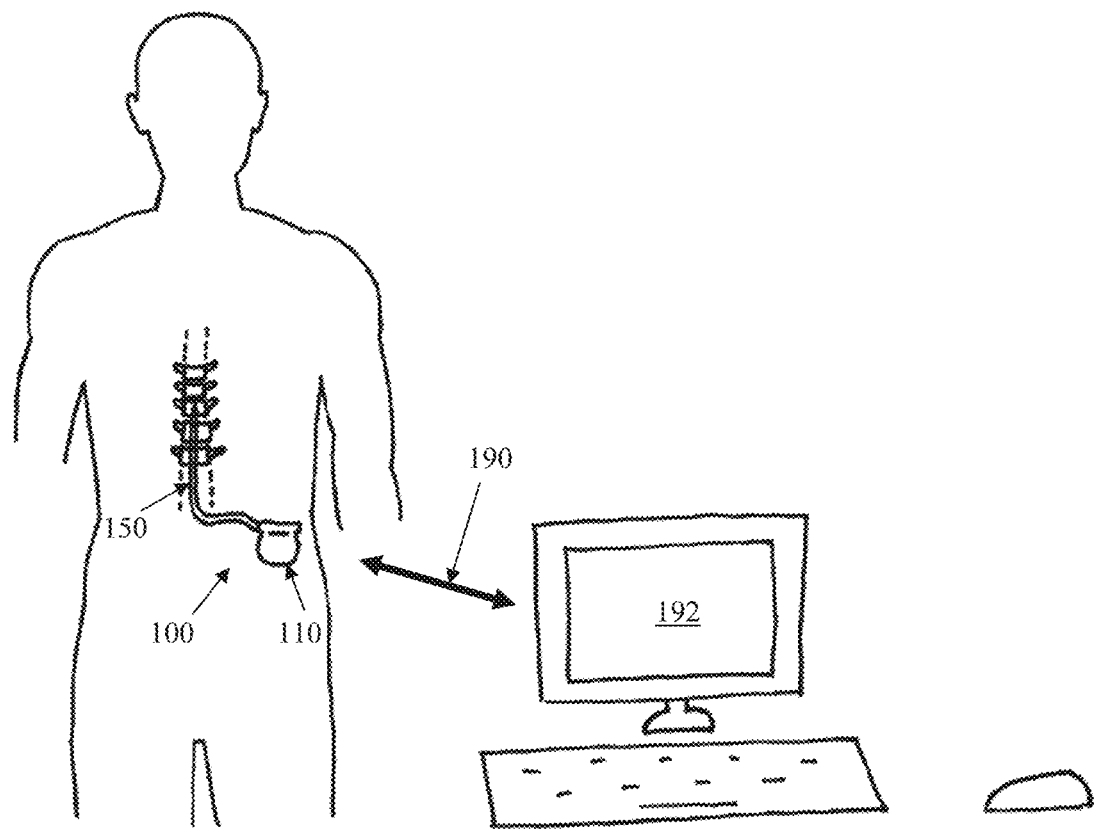
FIG. 1a schematically illustrates an implanted spinal cord stimulator suitable for implementing the present invention.

FIG. 1 schematically illustrates an implanted spinal cord stimulator 100 suitable for implementing the present invention. Stimulator 100 comprises an electronics module 110 implanted at a suitable location in the patient's lower abdominal area or posterior superior gluteal region, and an electrode assembly 150 implanted within the epidural space and connected to the module 110 by a suitable lead. Numerous aspects of operation of implanted neural device 100 are reconfigurable by an external control device 192. Moreover, implanted neural device 100 serves a data gathering role, with gathered data being communicated to external device 192.

Figure 1B:
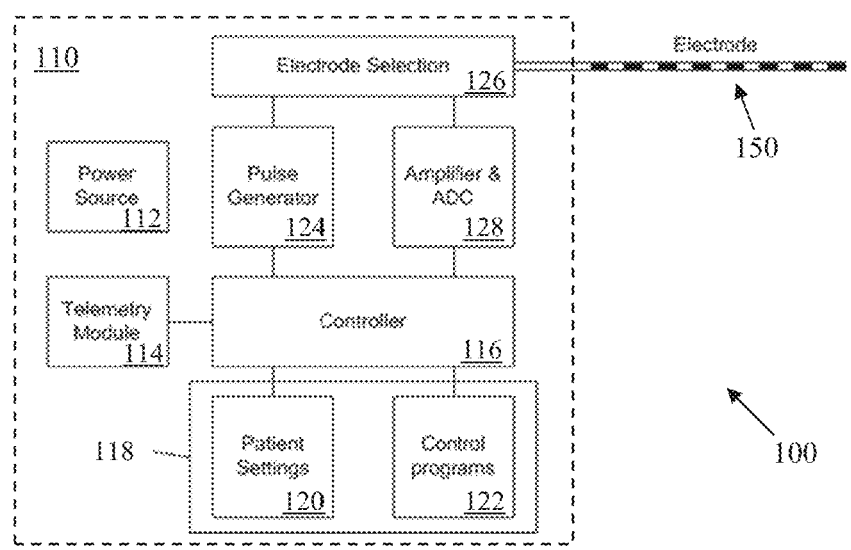
FIG. 1b is a block diagram of the implanted neurostimulator.

FIG. 1b is a block diagram of the implanted neurostimulator 100. Module 110 contains a battery 112 and a telemetry module 114. In embodiments of the present invention, any suitable type of transcutaneous communication 190, such as infrared (IR), electromagnetic, capacitive and inductive transfer, may be used by telemetry module 114 to transfer power and/or data between an external device 192 and the electronics module 110.

Module controller 116 has an associated memory 118 storing patient settings 120, control programs 122 and the like. Controller 116 controls a pulse generator 124 to generate stimuli in the form of current pulses in accordance with the patient settings 120 and control programs 122. Electrode selection module 126 switches the generated pulses to the appropriate electrode(s) of electrode array 150, for delivery of the current pulse to the tissue surrounding the selected electrode(s). Measurement circuitry 128 is configured to capture measurements of neural responses sensed at sense electrode(s) of the electrode array as selected by electrode selection module 126.

Figure 1C:
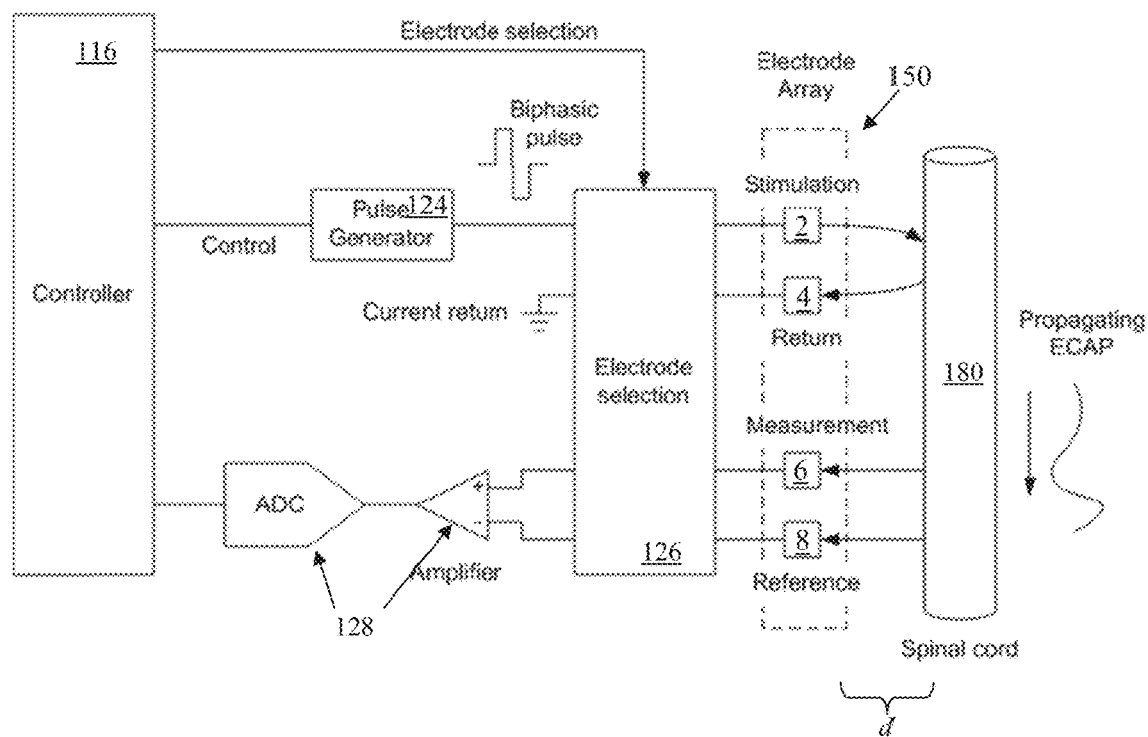
FIG. 1c is a schematic illustrating interaction of the implanted stimulator with a nerve.

FIG. 1c is a schematic illustrating interaction of the implanted stimulator 100 with a nerve 180, in this case the spinal cord however alternative embodiments may be positioned adjacent any desired neural tissue including a peripheral nerve, visceral nerve, parasympathetic nerve or a brain structure. Electrode selection module 126 selects a stimulation electrode 2 of electrode array 150 to deliver an electrical current pulse to surrounding tissue including nerve 180, and also selects a return electrode 4 of the array 150 for stimulus current recovery to maintain a zero net charge transfer.

Delivery of an appropriate stimulus to the nerve 180 evokes a neural response comprising a compound action potential which will propagate along the nerve 180 as illustrated, for therapeutic purposes which in the case of a spinal cord stimulator for chronic pain might be to create paraesthesia at a desired location. To this end the stimulus electrodes are used to deliver stimuli at 30 Hz. To fit the device, a clinician applies stimuli which produce a sensation that is experienced by the user as a paraesthesia. When the paraesthesia is in a location and of a size which is congruent with the area of the user's body affected by pain, the clinician nominates that configuration for ongoing use.

The device 100 is further configured to sense the existence and intensity of compound action potentials (CAPs) propagating along nerve 180, whether such CAPs are evoked by the stimulus from electrodes 2 and 4, or otherwise evoked. To this end, any electrodes of the array 150 may be selected by the electrode selection module 126 to serve as measurement electrode 6 and measurement reference electrode 8. Signals sensed by the measurement electrodes 6 and 8 are passed to measurement circuitry 128, which for example may operate in accordance with the teachings of International Patent Application Publication No. WO2012155183 by the present applicant, the content of which is incorporated herein by reference.

Figure 2A:
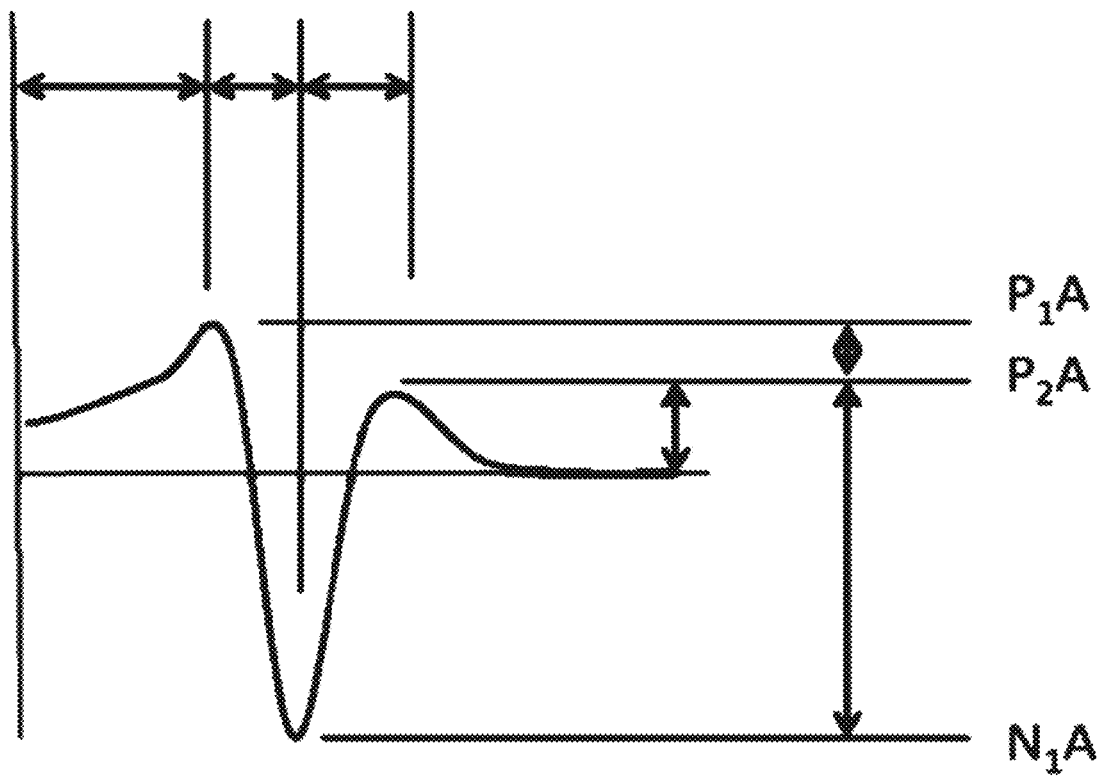
FIG. 2a illustrates the typical form of an electrically evoked compound action potential of a healthy subject.

FIG. 2a illustrates the typical form of an electrically evoked compound action potential of a healthy subject. The shape of the compound action potential shown in FIG. 2a is predictable because it is a result of the ion currents produced by the ensemble of axons generating action potentials in response to stimulation. The action potentials generated among a large number of fibres sum to form a compound action potential (CAP). The CAP is the sum of responses from a large number of single fibre action potentials. The CAP recorded is the result of a large number of different fibres depolarising. The propagation velocity is determined largely by the fibre diameter. The CAP generated from the firing of a group of similar fibres is measured as a positive peak potential P1, then a negative peak N1, followed by a second positive peak P2. This is caused by the region of activation passing the recording electrode as the action potentials propagate along the individual fibres. An observed CAP signal will typically have a maximum amplitude in the range of microvolts.

The CAP profile takes a typical form and can be characterised by any suitable parameter(s) of which some are indicated in FIG. 2a. The positions and amplitudes of the peaks can for example be used alone or in combination to generate a correlation between them and the state and severity of a central nervous system (CNS) disorder. Depending on the polarity of recording, a normal recorded profile may take an inverse form to that shown in FIG. 2a, i.e. having two negative peaks N1 and N2, and one positive peak P1.

Figure 2B:
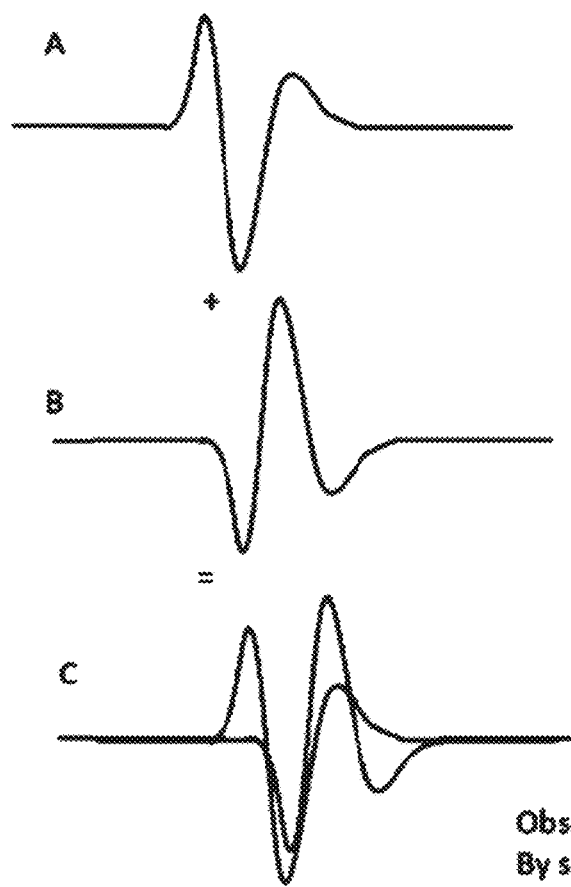
FIGS. 2b and 2c illustrate how the CAP manifests in the recording when using a differential recording arrangement with an epidural ground.
Figure 2C:
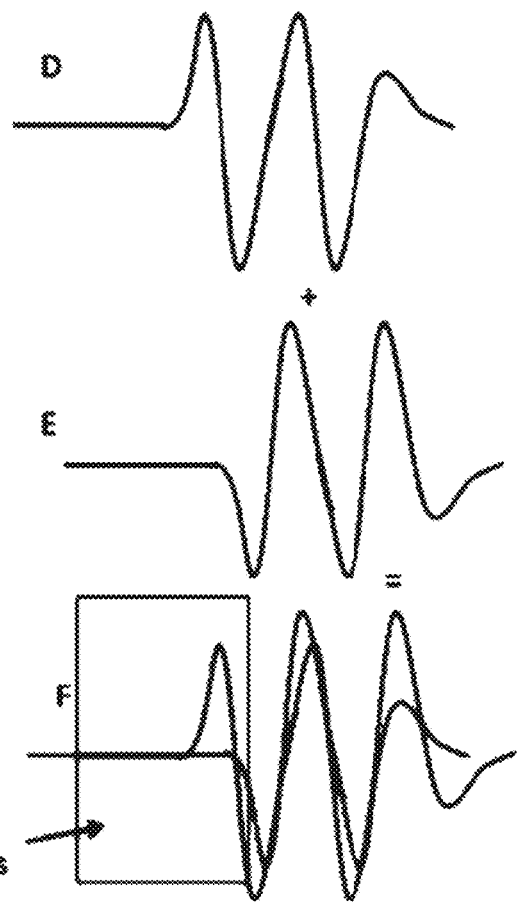

FIG. 2b illustrates how the CAP manifests in the recording, when using a differential recording arrangement with an epidural ground. In FIG. 2b a normal ECAP shape (A) is inverted and delayed by the propagation distance to the epidural ground electrode (B), and so the differential measure will look like the envelope of C. FIG. 2c shows the corresponding manifestation in relation to an anomalous CAP (D). The anomalous CAP has a strong doublet, which is inverted and delayed by the propagation distance to the epidural ground electrode (E), and so the differential measure will look like the envelope of F. As shown in FIG. 2c, and also being the case for FIG. 2b, the actual recording obtained typically does not include the first positive peak as it is obscured by the stimulus.

The present invention thus recognises that the shape or profile of the compound action potential reflects changes in the ion channel characteristics as a result of pathological or natural change.

Examples

Comparison of ECAP measurements from the dorsal column of a number of different human subjects was undertaken in order to identify systematic differences which relate to either genetic or pathological differences between subjects. Measurements of dorsal column evoked compound action potentials show distinct differences between the ECAP shapes measured at different electrodes along the array.

Figure 3:
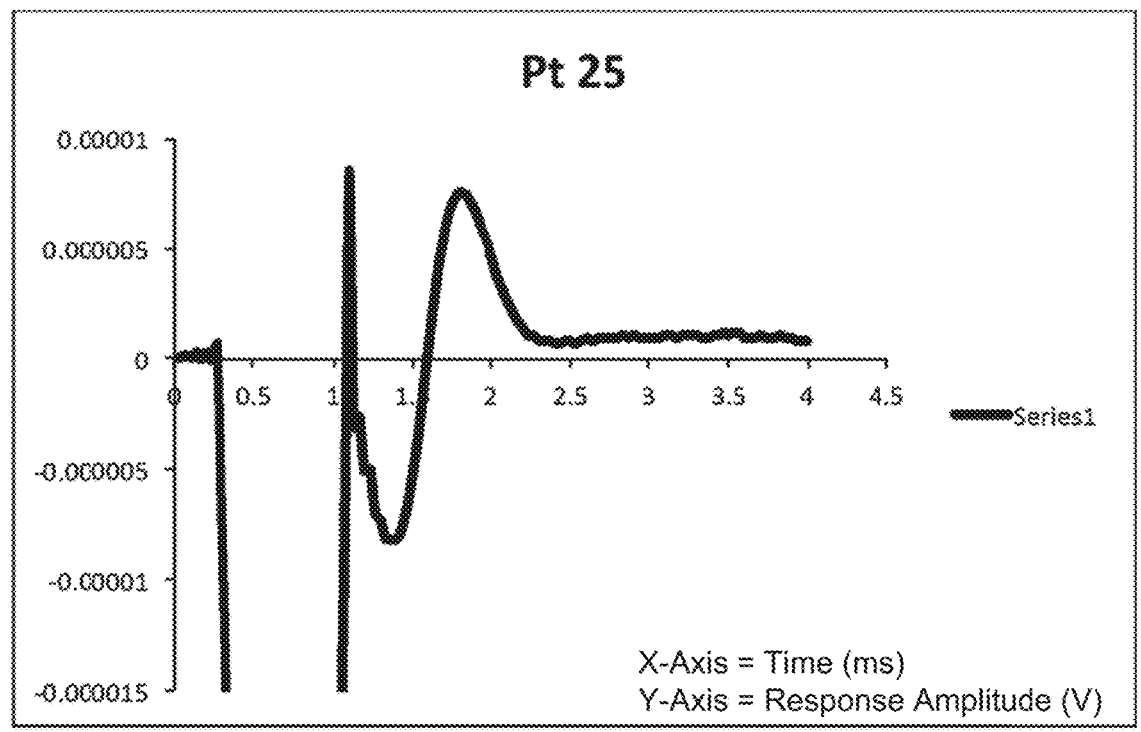
FIG. 3 illustrates an actual ECAP recording obtained from a subject having a normal neural state.

FIG. 3 shows a "normal" ECAP, being a triphasic P1, N1, P2 response, as obtained from "patient 25". The use of epidural ground inverts the N1 at a time when the response passes the ground electrode. As the recorded response of FIG. 3 exhibits no significant abnormalities as compared to the predicted response of FIG. 2, Patient 25 can be diagnosed as having no measurable neuropathic disease.

Figure 4:
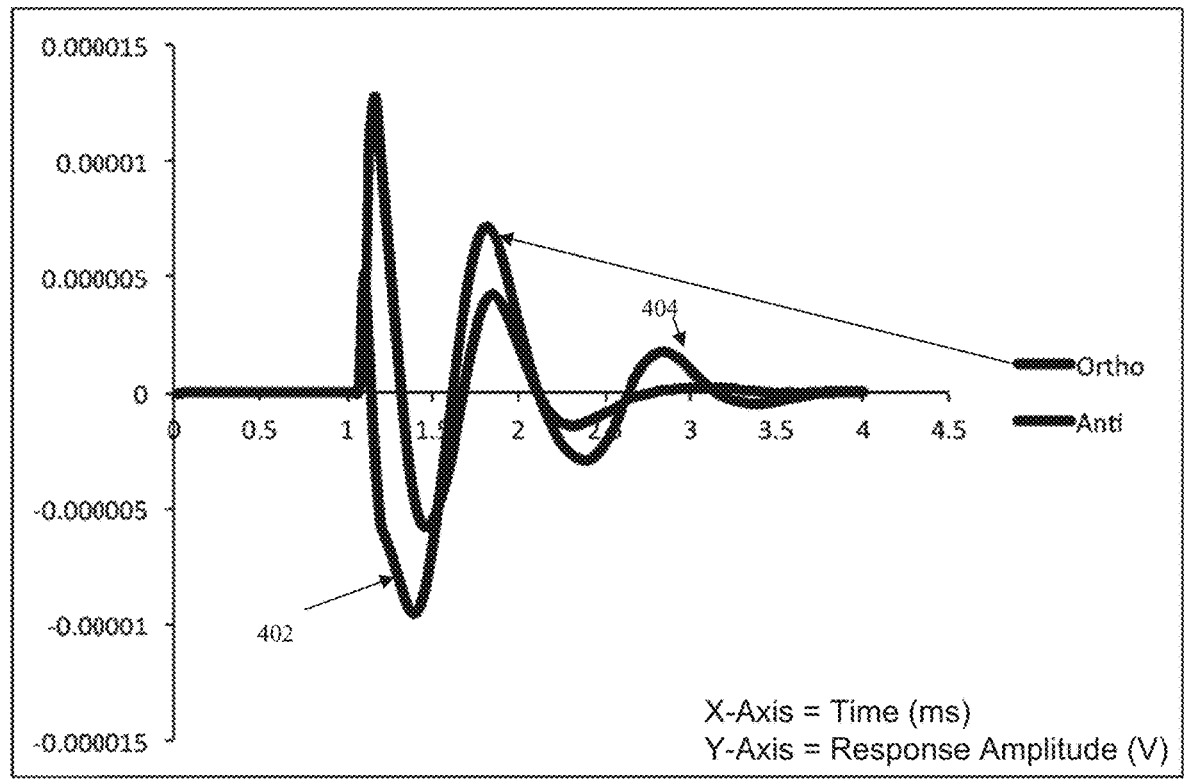
FIG. 4 illustrates anomalous ECAP recordings obtained from a subject suffering a neural disease.

In contrast, FIG. 4 shows data from patient 34, measured in both the orthodromic and antidromic directions at respective electrodes either side of the stimulus electrode, each spaced apart from the stimulus electrode by three electrodes. The N1 peak 402 is broader in the orthodromic direction, displays a faster rise time and is larger in amplitude. Moreover, an additional lobe 404 has emerged in the orthodromic response, in deviation from the expected response of FIG. 3. Any or all of these abnormalities may be detected and/or quantified in order to produce an automated diagnosis of the existence or severity of neural disease in patient 34. For example in some embodiments a measurement may be taken of the signal amplitude or power occurring within a time window covering the anomalous peak 404. When the amplitude or power in such a time window exceeds a threshold the response may be flagged as being anomalous.

Figure 5:
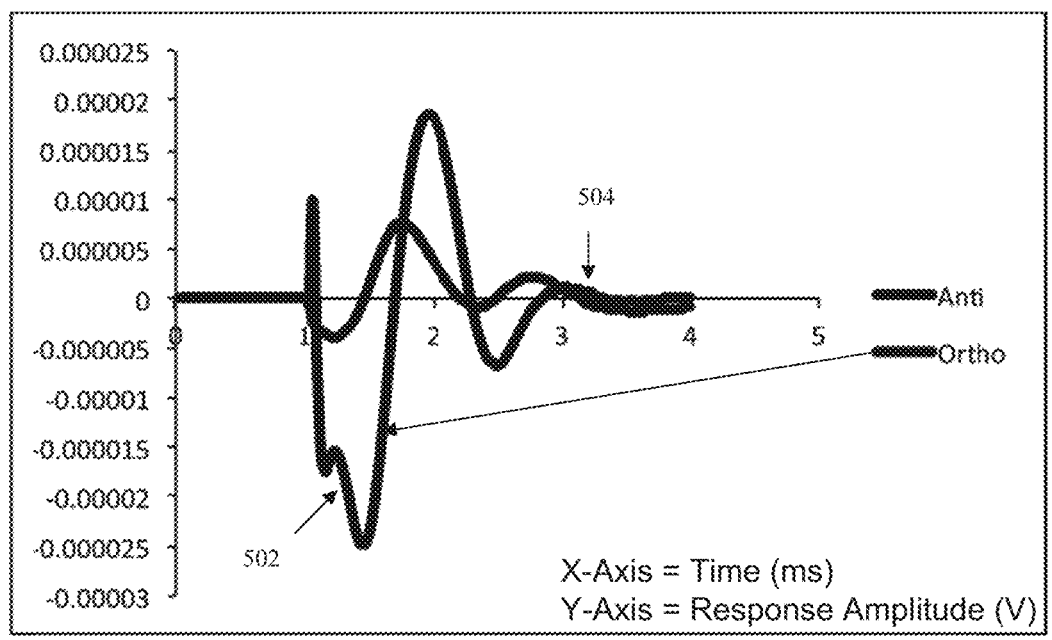
FIG. 5 illustrates anomalous ECAP recordings obtained from another subject suffering a neural disease.

FIG. 5 illustrates the recordings of the corresponding orthodromic and antidromic responses arising from patient 22. As seen at 502 in the N1 peak of the orthodromic response, the N1 peak 502 is broader in the orthodromic direction, displays a faster rise time and is larger in amplitude. An additional lobe 504 has emerged in the orthodromic response, in deviation from the expected response of FIG. 3. Thus patient 22 exhibits doublets which may be detected and/or quantified in order to produce an automated diagnosis of the existence or severity of neural disease in patient 22.

Figure 6:
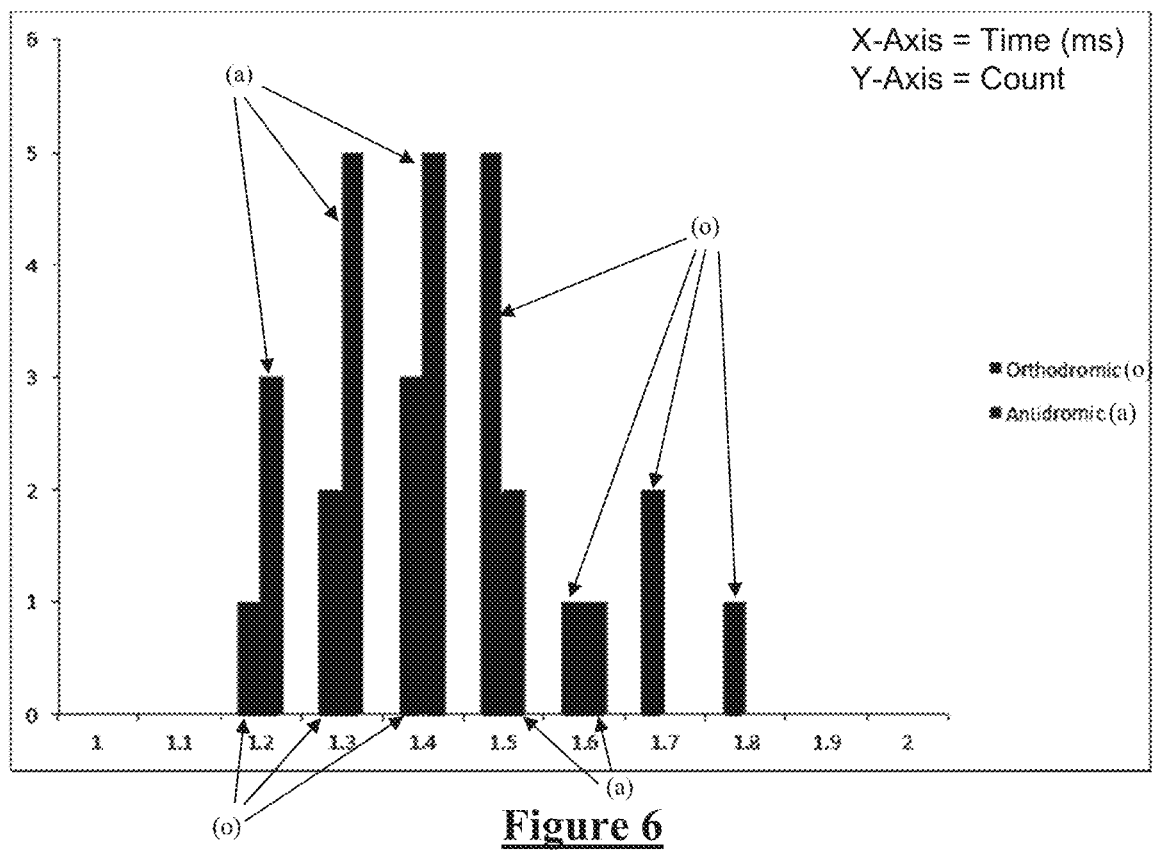
FIG. 6 is a plot of the differences between the N1, N2 peaks measured doublets.

FIG. 6 is a histogram of N1 peak latencies in ms, measured at the same stimulus electrode to recording electrode separation, for a large number of patients. This illustrates that N1 peak latency is predictable within quite a narrow time range as the peaks have quite a narrow spread over a large number of patients.

Figure 7:
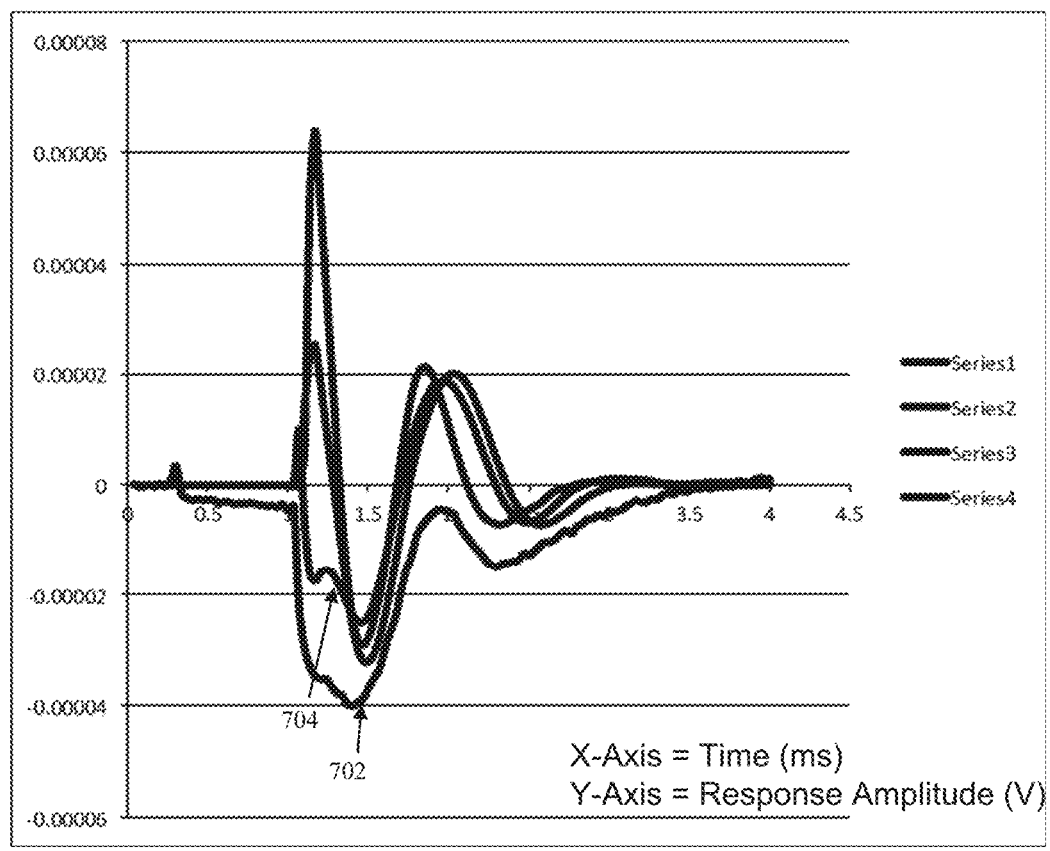
FIG. 7 shows the normalised antidromic responses from three patients plotted together.

FIG. 7 shows the normalised antidromic responses from three patients plotted together. The N1 peaks have very similar latencies. The peak shapes 702 and 704 are normal, noting the effects described in relation to FIGS. 2b and 2c.

Figure 8:
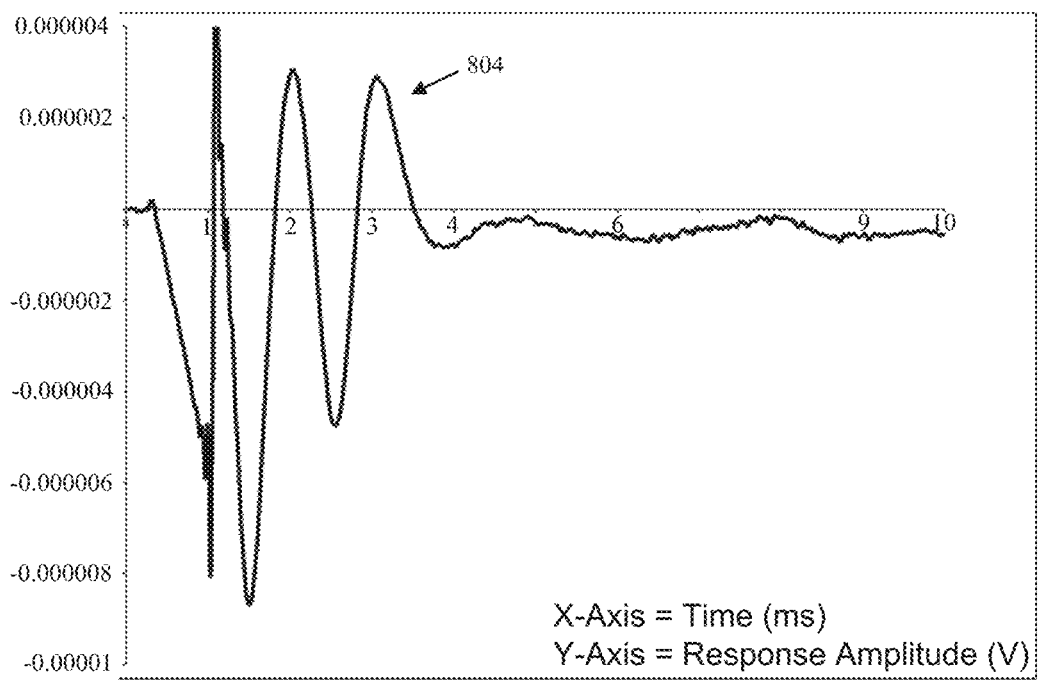
FIG. 8 shows an example of a large doublet response in the antidromic response of one patient.

FIG. 8 shows an example of a large doublet response in the antidromic response of one patient, illustrating that severity of the neural state can be distinguished, for example by comparing the normalised height of lobe 804 to say lobe 404 or 504.

Figure 9:
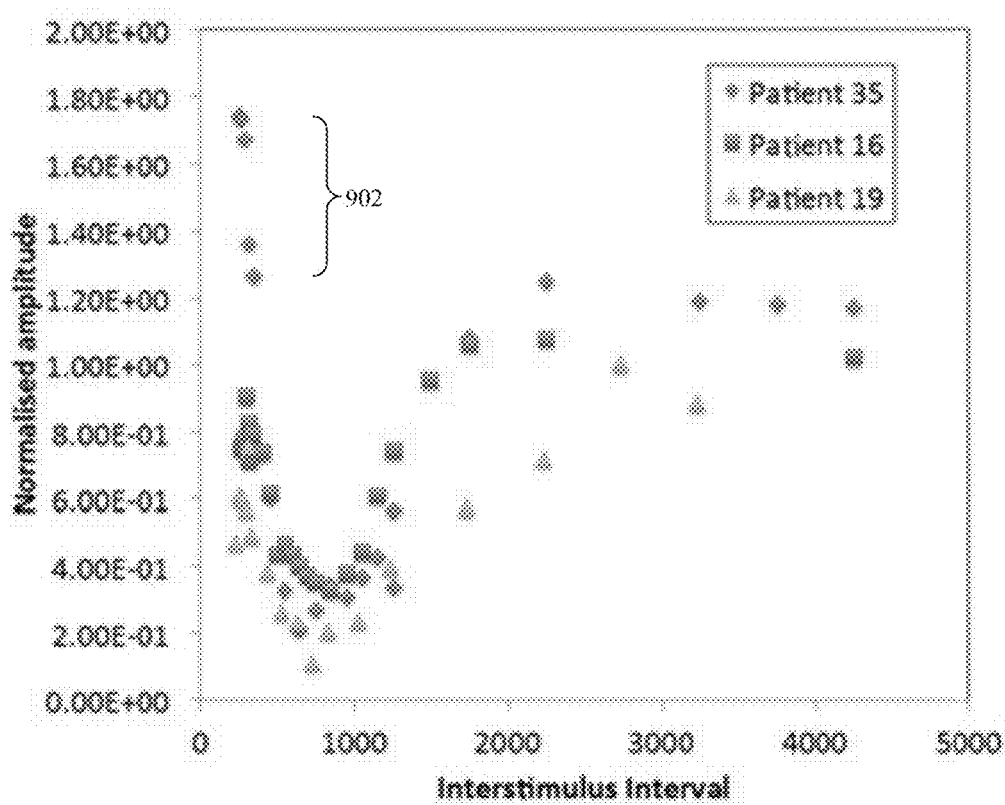
FIG. 9 is a plot of the normalized masker probe results for the refractory period of three patients.
Figure 10:
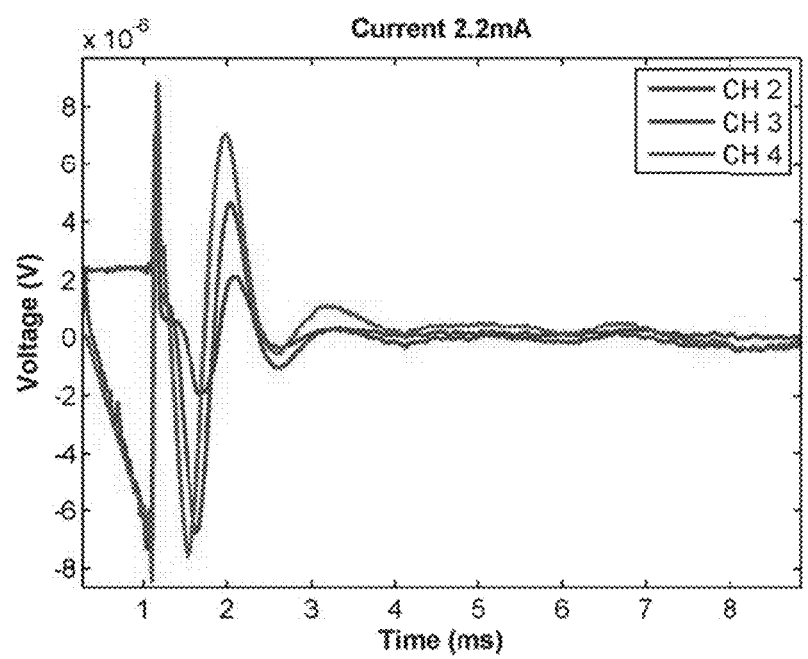
FIGS. 10-12 illustrate the relative severity of doublet formation for three respective patients.
Figure 11:
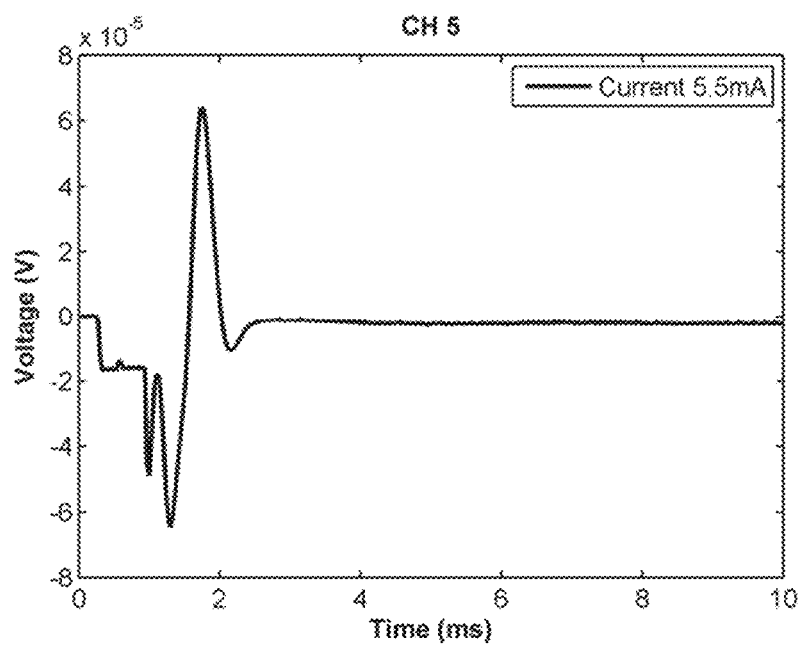
Figure 12:
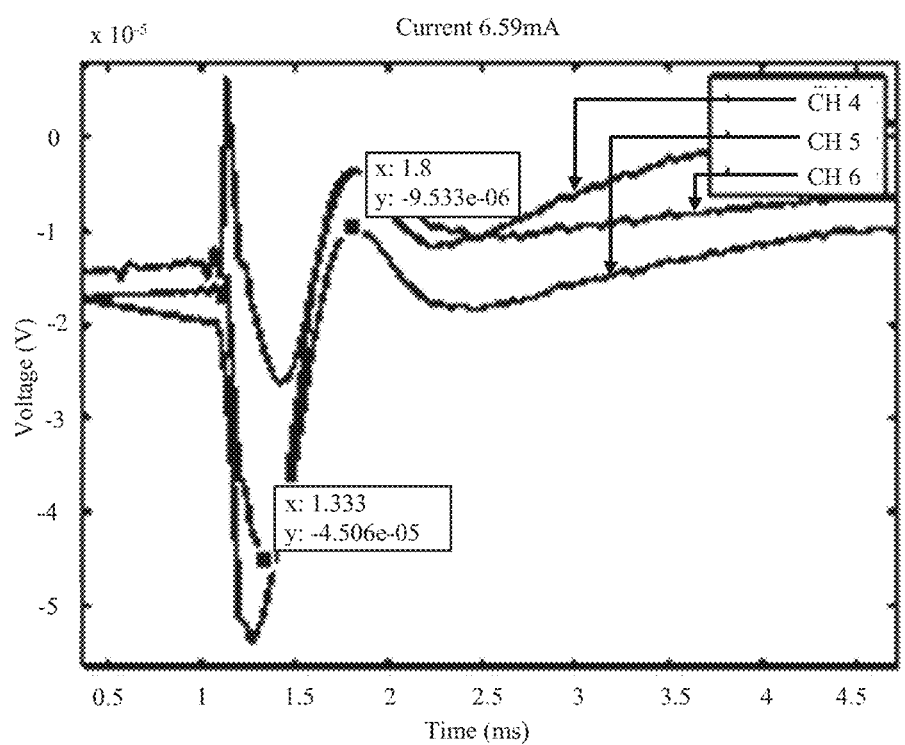

To explore the question of ectopic discharge, the refractory period was investigated using the "masker probe" techniques set forth in International Patent Application Publication No. WO2012/155189, the contents of which are incorporated herein by reference. FIG. 9 is a plot of the normalized masker probe results for 3 patients, denoted patient nos 16, 19 and 35 respectively. For patient 35 the masked amplitude was divided by the unmasked amplitude. To allow for differences in the measurement mode for patients 16 and 19, the results were normalized against the responses at ~5000 micro seconds inter-stimulus interval (ISI). In general the results are consistent between patients. As shown in FIGS. 10-12, the CAP profile of patient 35 had the largest double peaks or doublets of the three patients, and also at short ISI's of the order of 100-200 us patient 35 had the largest additional recruitment as indicated at 902. The data for patient 16 was collected with an 80 us pulse width, and so this will affect the additional recruitment at the short ISI's.

FIG. 10 illustrates the progression of CAP profile as the CAP travels away from the stimulus site, for patient 35. This indicates that the existence of an atypical CAP profile may best be detected by making recordings very close to the stimulus site. It is noted that the anomalous peaks propagate with distance, which indicates that they are neural responses from the same group or class of fibres. FIG. 11 shows a response obtained from patient 16, and FIG. 12 shows a response obtained from patient 19, revealing that of these three patients Patient 35 has the most severe doublet formation in their neural response.

There appears to be little consistency between the N1 latency and the appearance of the double response so N1 latency may not be a suitable parameter for diagnosing neural state.

Figure 13:
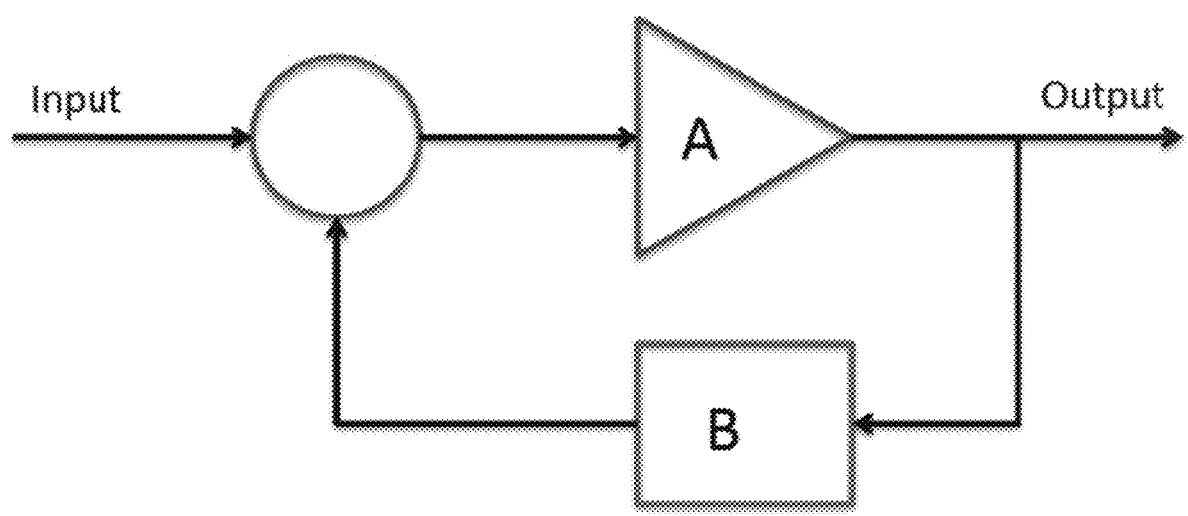
FIG. 13 illustrates a control system by which a therapy may be modified in accordance with one embodiment of the invention.

Some embodiments may provide for repeated assessment of the recorded response profile from time to time, for example throughout administration of a therapy, in order to assess disease state, disease progress, and therapy efficacy, and may be used to guide therapy modifications and optimisation over time. Therapy modifications may include modifications of dosage of a medicament and/or modification of a stimulus regime applied by a spinal column stimulator. FIG. 13 illustrates a control loop by which drug dosage or electrical stimuli dosage is adjusted in a dynamic manner, with the magnitude of the doublet (404, 504) being used as a control variable for a feedback loop.

It will he appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method of assessing a neural state of a subject, the method comprising:
    obtaining a recording of a compound action potential arising in neural tissue of the subject from one or more implanted sense electrodes of an implantable neurostimulator;
    providing to a processor of a control device the recording of the compound action potential;
    processing, by the processor, the recording to detect an anomaly in a profile of the recorded compound action potential by determining whether a peak in the recorded compound action potential has an atypically swift rate of rise;
    generating, by the processor, an indication regarding the neural state of the subject based on detected anomalies in the recorded compound action potential;
    outputting, by the processor, the indication regarding the neural state of the subject; and
    configuring, by the processor, the implantable neurostimulator using the indication regarding the neural state of the subject.

2. The method of claim 1 wherein the detection of an anomaly in the profile of the recorded compound action potential further comprises determining whether more than three peaks exist in the recorded compound action potential.

3. The method of claim 1 wherein the detection of an anomaly in the profile of the recorded compound action potential further comprises determining whether a peak in the recorded compound action potential is unexpectedly broad.

4. The method of claim 1 wherein the detection of an anomaly in the profile of the recorded compound action potential further comprises determining whether anomalous frequency components exist in the recorded compound action potential when assessed in the frequency domain.

5. The method of claim 1 wherein the detection of an anomaly in the profile of the recorded compound action potential further comprises:
    determining a degree of deviation of the profile of the recorded compound action potential from a predefined expected compound action potential profile; and
    comparing the degree of deviation with a predetermined threshold.

6. The method of claim 1 wherein the detection of an anomaly in the profile of the recorded compound action potential comprises identifying a locus of neuropathic pain by applying stimuli to first and second neural sites and determining which stimulus gives rise to greatest anomalies in a recorded compound action potential profile.

7. The method of claim 1 wherein configuring the implantable neurostimulator is performed intra-operatively to effect electrode array implantation site optimisation.

8. The method of claim 1 wherein configuring the implantable neurostimulator is performed during a programming stage in order to optimise electrode selection.

9. The method of claim 1 wherein configuring the implantable neurostimulator is performed intra-operatively during a sympathectomy procedure, in order to provide an intra-operative progressive indication of efficacy of the sympathectomy.

10. The method of claim 1, further comprising administering or modifying a therapy in a manner responsive to the indication regarding the neural state of the subject.

11. A neural state measurement system, comprising:
    an implantable neurostimulator, comprising:
        at least one implantable sense electrode;
        a telemetry module;
        a module controller; and
        a memory, where the memory comprises a control program capable of directing a processor to:
            obtain a recording of a compound action potential arising in neural tissue of a subject using the at least one implantable sense electrode; and
            provide the recording of the compound action potential to a processor of a control device; and
    the control device, where the processor of the control device is configured to:
        process the recording to detect an anomaly in a profile of the recorded compound action potential by determining whether a peak in the recorded compound action potential has an atypically swift rate of rise;
        generate, based on detected anomalies in the recorded compound action potential, an indication regarding the neural state of the subject;
        output the indication regarding the neural state of the subject; and
        configure the implantable neurostimulator using the indication regarding the neural state of the subject.

12. The neural state measurement system of claim 11, wherein the detection of an anomaly in the profile of the recorded compound action potential further comprises determining whether more than three peaks exist in the recorded compound action potential.

13. The neural state measurement system of claim 11, wherein the detection of an anomaly in the profile of the recorded compound action potential further comprises determining whether a peak in the recorded compound action potential is unexpectedly broad.

14. The neural state measurement system of claim 11, wherein the detection of an anomaly in the profile of the recorded compound action potential further comprises determining whether anomalous frequency components exist in the recorded compound action potential when assessed in the frequency domain.

15. The neural state measurement system of claim 11, wherein the detection of an anomaly in the profile of the recorded compound action potential further comprises:
  determining a degree of deviation of the profile of the recorded compound action potential from a predefined expected compound action potential profile; and
  comparing the degree of deviation with a predetermined threshold.

16. The neural state measurement system of claim 11 wherein the detection of an anomaly in the profile of the recorded compound action potential comprises identifying a locus of neuropathic pain by applying stimuli to first and second neural sites and determining which stimulus gives rise to greatest anomalies in a recorded compound action potential profile.

17. The neural state measurement system of claim 11, wherein configuring the implantable neurostimulator is performed intra-operatively to effect electrode array implantation site optimisation.

18. The neural state measurement system of claim 11, wherein configuring the implantable neurostimulator is performed during a programming stage in order to optimise electrode selection.

19. The neural state measurement system of claim 11, wherein configuring the implantable neurostimulator is performed intra-operatively during a sympathectomy procedure, in order to provide an intra-operative progressive indication of efficacy of the sympathectomy.

20. The neural state measurement system of claim 11, wherein the processor of the control device is further configured to administer or modify a therapy in a manner responsive to the indication regarding the neural state of the subject.

* * * * *